US009914756B2

(12) United States Patent
Beernink

(10) Patent No.: US 9,914,756 B2
(45) Date of Patent: Mar. 13, 2018

(54) NON-NATURALLY OCCURRING FACTOR H BINDING PROTEINS (FHBP) AND METHODS OF USE THEREOF

(71) Applicant: Children's Hospital & Research Center Oakland, Oakland, CA (US)

(72) Inventor: Peter T. Beernink, Walnut Creek, CA (US)

(73) Assignee: CHILDREN'S HOSPITAL & RESEARCH CENTER AT OAKLAND, Oakland, CA (US)

( * ) Notice: Subject to any disclaimer, the term of this patent is extended or adjusted under 35 U.S.C. 154(b) by 0 days.

(21) Appl. No.: 14/907,228

(22) PCT Filed: Aug. 1, 2014

(86) PCT No.: PCT/US2014/049465
§ 371 (c)(1),
(2) Date: Jan. 22, 2016

(87) PCT Pub. No.: WO2015/017817
PCT Pub. Date: Feb. 5, 2015

(65) Prior Publication Data
US 2016/0159865 A1    Jun. 9, 2016

Related U.S. Application Data

(60) Provisional application No. 61/861,662, filed on Aug. 2, 2013.

(51) Int. Cl.
*A61K 39/095* (2006.01)
*C07K 14/22* (2006.01)
*A61K 39/00* (2006.01)

(52) U.S. Cl.
CPC ............ *C07K 14/22* (2013.01); *A61K 39/095* (2013.01); *A61K 2039/53* (2013.01)

(58) Field of Classification Search
CPC .............. A61K 2039/53; A61K 39/095; A61K 2039/55505; A61K 39/00; A61K 39/39; A61K 2039/55566; A61K 47/48284; A61K 2039/575; C07K 14/22; C07K 14/195; C07K 14/4713; C07K 14/76; C07K 14/765; C07K 2319/00; A21D 8/00
See application file for complete search history.

(56) References Cited

U.S. PATENT DOCUMENTS

| 7,628,995 | B2 | 12/2009 | Bos et al. |
|---|---|---|---|
| 8,101,194 | B2 | 1/2012 | Zlotnick et al. |
| 8,968,748 | B2 | 3/2015 | Granoff et al. |
| 9,266,942 | B2 | 2/2016 | Granoff et al. |
| 2004/0167068 | A1 | 8/2004 | Zlotnick et al. |
| 2006/0171957 | A1 | 8/2006 | Pizza |
| 2006/0251670 | A1 | 11/2006 | Comanducci et al. |
| 2007/0026021 | A1 | 2/2007 | Fraser et al. |
| 2008/0248065 | A1 | 10/2008 | Granoff et al. |
| 2009/0035328 | A1 | 2/2009 | Granoff et al. |
| 2011/0256180 | A1 | 10/2011 | Beernink et al. |
| 2011/0318378 | A1 | 12/2011 | Beernink et al. |
| 2012/0107339 | A1 | 5/2012 | Grannof et al. |
| 2012/0288517 | A1 | 11/2012 | Beernink et al. |
| 2013/0022633 | A1 | 1/2013 | Banci et al. |
| 2013/0149326 | A1 | 6/2013 | Contorni et al. |
| 2013/0217859 | A1 | 8/2013 | Masignani et al. |
| 2014/0294886 | A1* | 10/2014 | Pizza .................. A61K 39/095 424/190.1 |

FOREIGN PATENT DOCUMENTS

| AU | 2013206190 A1 | 6/2013 |
|---|---|---|
| WO | WO99057280 | 11/1999 |
| WO | WO200152885 | 7/2001 |
| WO | WO2003063766 | 8/2003 |
| WO | WO04048404 | 10/2004 |
| WO | WO06024954 | 3/2006 |
| WO | WO06081259 | 8/2006 |
| WO | WO07060548 | 5/2007 |
| WO | WO09038889 | 3/2009 |
| WO | WO2009104097 | 8/2009 |
| WO | WO09114485 | 9/2009 |
| WO | WO10027872 | 3/2010 |
| WO | WO10028096 | 3/2010 |
| WO | WO2010028859 A1 | 3/2010 |
| WO | WO10046715 | 4/2010 |
| WO | WO10127172 | 11/2010 |
| WO | WO2013006055 A1 | 1/2013 |
| WO | WO2013006055 A8 | 1/2013 |
| WO | WO2013/078223 | 5/2013 |

OTHER PUBLICATIONS

Beernink, et al., Factor H Binding Protein. GenBank Direct Submission Accession ACJ45782 [online]. Nov. 23, 2008 [retrieved on Aug. 2, 2011], retrieved from the Internet:URL:http://www.ncbi.nlm.nih.gov/proteinacj45782, p. 1.

Beernink et al., (2010) "Impaired immunogenicity of a meningococcal factor H-binding protein vaccine engineered to eliminate factor h binding" *Clin Vaccine Immunol* 17(7):1074-1078.

Beernink, et al., (2006) "Rapid Genetic Grouping of Factor h-binding Protein (Genome-Derived neisserial antigen 1870), a Promising Group B Meningoccal Vaccine Candidate", *Clin. Vaccine Immunol.* 13(7):758-763.

(Continued)

*Primary Examiner* — S. Devi
(74) *Attorney, Agent, or Firm* — Shweta Chandra; Carol L. Francis; Bozicevic, Field & Francis LLP

(57) ABSTRACT

Non-naturally occurring factor H binding proteins derived from variant 3 fHbp that can elicit antibodies that are bactericidal for at least one strain of *N. meningitidis*, and methods of use of such proteins, are provided. In certain embodiments, a non-naturally occurring factor H binding protein (fHbp) derived from a naturally occurring variant 3 fHbp is disclosed. The non-naturally fHbp may include a substitution of the histidine at position 223 of the naturally occurring variant 3 fHbp with an amino acid selected from the group consisting of arginine, lysine, phenylalanine, tyrosine, or tryptophan, wherein the numbering of position 223 is based on the numbering of the mature fHbp ID 1. The non-naturally occurring fHbp may have a lower affinity for human factor H (fH) than fHbp ID 79.

16 Claims, 11 Drawing Sheets

(56) References Cited

OTHER PUBLICATIONS

Beernink. et al., "Bactericidal Antibody Responses Induced by Meningococcal Recombinant Chimeric Factor H-Binding Protein Vaccines", Infection and Immunity, 2008, 76(6):2568-2575.
Beernink, et al., "Fine Antigenic Specificity and Cooperative Bactericidal Activity of Monoclonal Antibodies Directed at the Meningococcal Vaccine Candidate Factor H-Binding Protein", Infection and Immunity, 2008, 76(9):4232-4940.
Beernink, et al., "Prevalence of Factor H-Binding Protein Variants and NadA Among Meningococcal Group B Isolates from the United States: Implications for the Development of a Multicomponent Group B Vaccine", Journal of Infectious Disease, 2007, 195(10):1472-1479.
Beernink, et al., The Modular Architecture of Meningococcal Factor H-Binging Protein, Microbiology, 2009, 155:2873-2883.
Beernink, et al., "A Region of the N-Terminal Domain of Meningococcal Factor H-Binding Protein that Elicits Bactericidal Antibody Across Antigenic Variant Groups", Molecular Immunology, 2009, 46(8-9):1647-1653.
De Filippis, et al., Factor H Binding Protein. GenBank Direct Submission Accession ACZ93290 [online]. Dec. 15, 2009 ]retrieved on Aug. 2, 2011], retrieved from the Internet:URL:http://www.ncbi.nlm.nih.gov/protein/acz93290, p. 1.
De Filippis, et al., Factor H Binding Protein. Gen Bank Direct Submission Accession ACZ93150 [online]. Dec. 15, 2009 [retrieved on Aug. 2, 2011], retrieved from the internet:URL:http://www.ncbi.nlm.nih.gov/protein/acz93150,p. 1.
Fukasawa, et al., Immune Response to Naitive NadA from *Neisseria meningitidis* and its Expression in Clinical Isolates in Brazil, Journal of Medical Microbiology, 2003, 52:121-125.
Davila et al., (2010) "Genome-wide association study identifies variants in the CFH region associated with host susceptibility to meningococcal disease" *Nat Genetics* 42(9):772-776. doi:10.1038/ng.640.
Fletcher, et al., (2004) "Vaccine potential of the *Neisseria meningitidis* 2086 lipoprotein" *Infect Immun.* 72(4):2088-2100.
GenBank Accession No. AY548370 "Neisseria meningitidis strain H44/76 lipoprotein (gna1870) gene, complete cds" (AAT01289.1) (from N. meningitidis strain H44/76), dated May 1, 2004.
GenBank Accession No. AY548371 "Neisseria meningitidis strain CU385 lipoprotein (gna1870) gene, complete cd" (AAT01290.1) (from N. meningitidis strain CU385), dated May 1, 2004.
GenBank Accession No. AY548372 "Neisseria meningitidis strain BZ83 lipoprotein GNA1870 (gna1870) gene, complete cd" (AAS56915.1) (from N. meningitidis strain BZ83), dated Apr. 22, 2004.
GenBank Accession No. AY548373 "Neisseria meningitidis strain 4243 lipoprotein GNA1870 (gna1870) gene, complete cd" (AAS56916.1) (from N. meningitidis strain 4243), dated Apr. 22, 2004.
GenBank Accession No. AY548374 "Neisseria meningitidis strain M6190 lipoprotein GNA1870 (gna1870) gene, complete cd" (AAS56917.1) (from N. meningitidis strain M6190), dated Apr. 22, 2004.
GenBank Accession No. AY548375 "Neisseria meningitidis strain N98/254 lipoprotein GNA1870 (gna1870) gene, complete cd" (AAS56918.1) (from N. meningitidis strain NZ98/254), dated Apr. 22, 2004.
GenBank Accession No. AY548376 "Neisseria meningitidis strain M1390 lipoprotein GNA1870 (gna1870) gene, complete cds" (AAS56919.1) (from N. meningitidis strain M1390), dated Apr. 22, 2004.
GenBank Accession No. AY548377 "Neisseria meningitidis strain M4105 lipoprotein GNA1870 (gna1870) gene, complete cd" (AAS56920.1) (fHbp ID 4 from N. meningitidis strain M4105), dated Apr. 22, 2004.

GenBank Accession No. NC_003112, "Neisseria meningitidis MC58, complete genom" GeneID: 904318 (NCBI Ref. NP_274866), fHbp ID 1 from N. meningitidis strain MC58, ), dated May 24, 2010.
GenBank Accession No. NP_000177 (P08603), and its encoding nucleic acid as NM_000186, "complement factor H isoform a precursor [*Homo sapiens*]" dated Mar. 21, 2010.
Giuliani, et al., (2005) "The region comprising amino acids 100 to 255 of *Neisseria meningitidis* lipoprotein GNA 1870 elicits bactericidal antibodies" Infect. Immun. 73(2):1151-1160.
Goldschneider, et al., (1969) "Human Immunity to the Meningococcus: I. The Role of the Humoral Antibodies" *J. Exp. Med.* 129(6):1307-1326.
Granoff, et al., (1998) "Bacterial Monoclonal Antibodies That Define Unique Meningococcal B Polysaccharide Epitopes That Do Not Cross-React with Human Polysialic Acid" *J. Immunol.* 160(10):5028-5036.
Granoff, et al., (2009) "Binding of complement factor H (fH) to Neisseria meningitidis is specific for human fH and inhibits complement activation by rat and rabbit sera" *Infect. Immun.* 77(2):764-769.
Lewis, et al., The Meningococcal Vaccine Candidate Neisserial Surface Protein a (NspA) Binds to Factor H and Enhances Meningococcal Resistance to Complement, Plos Pathogens, 2010, 6(7):1-20.
Madico, et al., "The Meningococcal Vaccine Candidate GNA1870 Binds the Complement Regulatory Protein Factor H and Enhances Serum Resistance", 2006, The Journal of Immunology, 177:501-510.
Madico, et al., Factor H Binding Protein. GenBank Direct Submission Accession ABC59063 [online], Jun. 20, 2006 [retrieved on Aug. 2, 2011], retrieved from the Internet:URL:http://www.ncbi.nlm.nih.gov/protein/abc59063, p. 1.
Masignani, et al., "Vaccination against Neisseria meningitides Using Three Variants of the Lipoprotein GNA1879,"Journal Exp. Med., 2003, 197(6):789-799.
McDowell, et al., "Demonstration of the Involvement of Outer Surface Protein E Coiled Coil Structure and Higher Order Structural Elements in the Binding of Infection-Induced Antibody and the Complement-Regulatory Protein, Factor H", Journal of Immunology, 2004, vol. 173, pp. 7471-7480.
Maslanka, et al., "Standardization and a Multilaboratory Comparison of Neisseria Meningitidis Serogroup A and C Serum Bactericidal Assays", Clinical Diagnostic Laboratory Immunology, 1997, 4(2):156-157.
Murphy, et al., Factor H Binding Protein Variant A72_001. GenBank Direct Submission Accession ACI46937 [online]. Aug. 4, 2009 [retrieved from the internet]:URL:http://www.ncbi.nim.nih.gov/protein/aci46937, p. 1.
Ngampasutadol et al., "Human Factor H Interacts Selectively with Neisseria Gonorrhoeae and Results in Species-Specific Complement Evasion", The Journal of Immunology, 2008, 180(5):3426-3435.
Ngampasutadol et al., "A Novel Interaction Between Factor H SCR 6 and the Meningococcal Vaccine Candidate GNA 1870: Implications for Meningococcal Pathogenesis and Vaccine Development", Molecular Immunology, 2007, 44(1-3):220.
Pajon, et al., (2010) "Frequency of factor H-binding protein modular groups and susceptibility to cross-reactive bactericidal activity in invasive meningococcal isolates" *Vaccine* 28(9):2122-2129.
Scarselli, et al., (2009) "Epitope mapping of a bactericidal monoclonal antibody against the factor H binding protein of Neisseria meningitidis" *J. Mol. Biol.* 386(1):97-108.
Schneider, et al., "Neisseria Meningitides Recruits Factor H Using Protein Mimicry of Host Carbohydrates", Nature, 2009, 458:890-895.
Schneider, et al., "Supplemental Methods for Neisseria Meningitides Recruits Factor H Using Protein Mimicry of Host Carbohydrates", Nature, 2009, 1-17.

(56) References Cited

OTHER PUBLICATIONS

Shaughnessy, et al., (2009) "Functional comparison of the binding of factor H short consensus repeat 6 (SCR 6) to factor H binding protein from Neisseria meningitidis and the binding of factor H SCR 18 to 20 to Neisseria gonorrhoeae porin" *Infect. Immun*77(5):2094-2103.

Tettelin, et al., Uniprot Q9JXV4 [online] Oct. 1, 2000 [retrieved on Aug. 2, 2011], retrieved from the Internet: URL:http://www.uniprot.org/uniprot/Q9JXV4.txt, p. 1.

Welsch, et al., Complement-Dependent Synergistic Bactericidal Activity of Antibodies Against Factor H-Binding Protein, a Sparsely Distributed Meningococcal Vaccine Antigen, The Journal of Infectious Disease, 2008, 197:1053-61.

Welsch, et al., "Protective Activity of Monoclonal Antibodies to Genome-Derived Neisserial Antigen 1870, a Neisseria Meningitidis Candidate Vaccine", Journal of Immunology, 2004, 172:5606-5615.

Welsch, et al., Lipoprotein GNA1870. GenBank Direct Submission Accession AAS56918 [online], Apr. 22, 2004 [retrieved on Aug. 2, 2011], retrieved from the Internet:<URL:http://www.ncbi.nlm.nih.gov/protein/AAS56918, p. 1.

Dunphy, et al., "Effect of Factor H-Binding Protein Sequence Variation on Factor H Binding and Survival of Neisseria meningitidis in Human Blood", 2011, Infection and Immunity, vol. 79, No. 1, pp. 353-359.

Seib, et al., "Characterization of Diverse Subvariants of the Meningococcal Factor H (fH) Binding Protein for Their Ability to Bind fH, to Mediate Serum Resistance, and to Induce Bactericidal Antibodies", 2011, Infection and Immunity, vol. 79, No. 2, pp. 970-981.

Johnson et al., "Design and Evaluation of Meningococcal Vaccines through Structure—Based Modification of Host and Pathogen Molecules", PLOS Pathogens (2012) 8(10): e1002981.

Konar et al., "A Mutant Library Approach to Identify Improved Meningococcal Factor H Binding Protein Vaccine Antigens," PLoS One. Jun. 9, 2015, 10(6):e0128185.

Pajon et al., Design of meningococcal factor H binding protein mutant vaccines that do not bind human complement factor H, Infect Immun. Aug. 2012, 80(8):2667-77.

Skolnick et al., "From genes to protein structure and function: novel applications of computational approaches in the genomic era", Trends in Biotechnology, 18:34-39, 2000.

Lazar et al "Transforming Growth Factor α: Mutation of Aspartic Acid 47 and Leucine 48 Results in Different Biological Activities", Mol. Cellular Biol., 8(3):1247-1252, 1988.

Beernink et al., In: Program and Abstract Guide, 17th International Pathogenic Neisseria Conference, Banff, Alberta, Canada, p. 58, #OM42, Sep. 11-16, 2010.

Borrow et al., "Serological Basis for Use of Meningococcal Serogroup C Conjugate Vaccines in the United Kingdom: Reevaluation of Correlates of Protection", Infect. Immun. (2001) 69(3):1568-1573.

Vu et al., "A Broadly Cross-Reactive Monoclonal Antibody Against an Epitope on the N-terminus of Meningococcal fHbp",Scientic Reports (2012) 2(341):1-8.

Beernink, P.T., et al., Abstracts of 16th International Pathogenic Neisseria Conference, Rotterdam, Netherlands, p. 194, #P126, Sep. 7-12, 2008.

Lazar, E., et al., "Transforming Growth Factor α: Mutation of Aspartic Acid 47 and Leucine 48 Results in Different Biological Activities," Mol. Cellular Biol. (1988) 8:1247-1252.

Morrison, K.L., et al., "Combination alanine-scanning," Curr. Opin. Chem. Biol. (2001) 5:302.307.

Genbank Accession No. AAW88802, Factor H binding protein from Neisseria Gonorrhoeae (strain ATCC 700825/FA 1090) Mar. 15, 2005.

* cited by examiner

FIGURE 4

```
fHbpID59   CSSGGGGSGSGGGVAADIGTGLAIALTTPLDHKDKGLKSLTLEDSIPQNGTLTLSAQGAEK  60
fHbpID31   CSSGGGGSGSGGGVAADIGTGLAIALTTPLDHKDKGLKSLTLEDSIPQNGTLTLSAQGAEK  60
fHbpID79   CSSGGGGSGSGGGVAADIGTGLADALTTPLDHKDKGLKSLTLEDSIPQNGTLTLSAQGAEK  60
fHbpID85   CSSGGGGSGSGGGVAADIGTGLADALTTPLDHKDKGLKSLTLEDSIPQNGTLTLSAQGAEK  60
fHbpID72   CSSGGGGS--GGVAADIGTGLADALTTPLDHKDKGLKSLTLEDSIPQNGTLTLSAQGAEK  58
fHbpID84   CSSGGGGSGSGGGVAADIGTGLADALTAPLDHKDKGLKSLTLEDSIPQNGTLTLSAQGAEK  60
fHbpID70   CSSGGGGSGGGGGVAADIGTGLADALTAPLDHKDKGLKSLTLEDSIPQNGTLTLSAQGAEK  60
fHbpID46   CSSGGGGSGGGGGVAADIGTGLADALTAPLDHKDKGLKSLTLEDSIPQNGTLTLSAQGAEK  60
fHbpID99   CSSGGGGSGGGGGVAADIGTGLADALTAPLDHKDKGLKSLTLEDSIPQNGTLTLSAQGAEK  60
fHbpID28   CSSGGGGSGGGGGVAADIGTGLADALTAPLDHKDKGLKSLTLEDSIPQNGTLTLSAQGAEK  60
fHbpID29   CSSGGGGSGGGGGVAADIGAGLADALTAPLDHKDKGLKSLTLEDSIPQNGTLTLSAQGAEK  60
fHbpID30   CSSGGGGSGGGGGVAADIGAGLADALTAPLDHKDKGLKSLTLEDSIPQNGTLTLSAQGAEK  60
fHbpID64   CSSC---SGGCCGVAADIGTCLADALTAPLDHKDKCLKSLTLEDSIPQNCTLTLSAQGAEK  57
fHbpID76   CSSGG---GSGGIAADIGTGLADALTAPLDHKDKGLKSLTLEDSIPQNGTLTLSAQGAEK  58
fHbpID45   CSSGGSG--SGGGVAADIGTGLADALTAPLDHKDKGLKSLTLEDSISQNGTLTLSAQGAEK  59
fHbpID47   CSSGG----GGVAADIGAGLADALTAPLDHKDKGLKSLTLEDSISQNGTLTLSAQGAEK  55
fHbpID82   CSSGG----GGVAADIGAGLADALTAPLDHKDKGLKSLTLEDSIPQNGTLTLSAQGAEK  55
fHbpID1    CSSGG----GGVAADIGAGLADALTAPLDHKDKGLQSLTLDQSVRKNEKLKLAAQGAEK  55
           ****     ** ******* *** *** ******* ***** *   *  * *****
```

FIGURE 5A

```
fHbpID59   TFKAGDKDNSLNTGKLKNDKISREDFVQKIEVDGQTITLASGEFQIYKQDHSAVVALQIE  120
fHbpID31   TFKAGDKDNSLNTGKLKNDKISREDFVQKIEVDGQTITLASGEFQIYKQDHSAVVALQIE  120
fHbpID75   TFKAGDKDNSLNTGKLKNDKISREDFVQKIEVDGQTITLASGEFQIYKQDHSAVVALQIE  120
fHbpID85   TFKAGDKDNSLNTGKLKNDKISREDFVQKIEVDGQTITLASGEFQIYKQDHSAVVALQIE  120
fHbpID72   TFKAGDKDNSLNTGKLKNDKISREDFVQKIEVDGQTITLASGEFQIYKQDHSAVVALQIE  118
fHbpID84   TFKAGDKDNSLNTGKLKNDKISRFDFVQKIEVDGQTITLASGEFQIYKQDHSAVVALQIE  120
fHbpID70   TFKAGDKDNSLNTGKLKNDKISREDFVQKIEVDGQTITLASGEFQIYKQDHSAVVALQIE  120
fHbpID46   TFKAGDKDNSLNTGKLKNDKISREDFVQKIEVDGQTITLASGEFQIYKQDHSAVVALQIE  120
fHbpID99   TFKAGDKDNSLNTGKLKNDKISREDFVQKIEVDGQTITLASGEFQIYKQNHSAVVALQIE  120
fHbpID28   TFKAGDKDNSLNTGKLKNDKISREDFVQKIEVDGQTITLASGEFQIYKQDHSAVVALQIE  120
fHbpID29   TFKAGDKDNSLNTGKLKNDKISREDFVQKIEVDGQTITLASGEFQIYKQNHSAVVALQIE  117
fHbpID30   TFKAGDKDNSLNTGKLKNDKISREDFVQKIEVDGQTITLASGEFQIYKQNHSAVVALQIE  120
fHbpID64   TFKAGDKDNSLNTGKLKNDKISREDFVQKIEVDGQTITLASGEFQIYKQDHSAVVALQIE  120
fHbpID76   TFKVGDKDNSLNTGKLKNDKISREDFVQKIEVDGQTITLASGEFQIYKQDHSAVVALQIE  117
fHbpID45   TFKAGDKDNSLNTGKLKNDKISREDFVQKIEVDGQTITLASGEFQIYKQDHSAVVALQIE  118
fHbpID47   TFKVGDKDNSLNTGKLKNDKISREDFVQKIEVDGQTITLASGEFQIYKQDHSAVVALQIE  119
fHbpID82   TFKAGDKDNSLNTGKLKNDKISREDFVQKIEVDGQTITLASGEFQIYKQNHSAVVALQIE  115
fHbpID1    TYGNGD----SLNTGKLKNDKVSRFDFIRQIEVDGQLITLESGEFQVYKQSHSALTAFQTE  112
              *    **********:*** **:**:*::****   * : ****:**:::*:: :* *
```

FIGURE 5B

| | | |
|---|---|---|
| fHbpID59 | KINNPDKIDSLINQRSFLVSGLGGEHTAFNQLP-GGKAEYHGKAFSSDDAGGKLTYTIDF | 179 |
| fHbpID31 | KINNPDKIDSLINQRSFLVSGLGGEHTAFNQLP-GGKAEYHGKAFSSDDAGGKLTYTIDF | 179 |
| fHbpID79 | KINNPDKIDSLINQRSFLVSGLGGEHTAFNQLP-GGKAEYHGKAFSSDDAGGKLTYTIDF | 179 |
| fHbpID85 | KINNPDKIDSLINQRSFLVSGLGGEHTAFNQLP-SGKAEYHGKAFSSDDAGGKLTYTIDF | 177 |
| fHbpID72 | KINNPDKIDSLINQRSFLVSGLGGEHTAFNQLP-GGKAEYHGKAFSSDDAGGKLTYTIDF | 179 |
| fHbpID84 | KINNPDKIDSLINQRSFLVSGLGGEHTAFNQLP-GGKAEYHGKAFSSDDAGGKLTYTIDF | 179 |
| fHbpID70 | KINNPDKIDSLINQRSFLVSGLGGEHTAFNQLP-GGKAEYHGKAFSSDDAGGKLTYTIDF | 179 |
| fHbpID46 | KINNPDKIDSLINQRSFLVSGLGGEHTAFNQLP-GGKAEYHGKAFSSDDPNGRLHYSIDF | 179 |
| fHbpID99 | KINNPDKIDSLINQRSFLVSGLGGEHTAFNQLP-GGKAEYHGKAFSSDDPNGRLHYSIDF | 179 |
| fHbpID28 | KINNPDKIDSLINQRSFLVSGLGGEHTAFNQLP-GGKAEYHGKAFSSDDPNGRLHYSIDF | 179 |
| fHbpID29 | KINNPDKTDSLINQRSFLVSGLGGEHTAFNQLP-GGKAEYHGKAFSSDDPNGRLHYSIDF | 179 |
| fHbpID30 | KINNPDKIDSLINQRSFLVSGLGGEHTAFNQLP-GDKAEYHGKAFSSDDPNGRLHYTIDF | 176 |
| fHbpID64 | KINNPDKIDSLINQRSFLVSGLGGEHTAFNQLP-GGKAEYHGKAFSSDDPNGRLHYTIDF | 177 |
| fHbpID76 | KINNPDKIDSLINQRSFLVSGLGGEHTAFNQLP-SGKAEYHGKAFSSDDAGGKLTYTIDF | 178 |
| fHbpID45 | KINNPDKIDSLINQRSFLVSGLGGEHTAFNQLP-GGKAEYHGKAFSSDDAGGKLTYTIDF | 174 |
| fHbpID47 | KINNPDKIDSLINQRSFLVSGLGGEHTAFNQLP-VGKAEYHGKAFSSDDAGGKLTYTIDF | 174 |
| fHbpID82 | QIQDSEHSGRMVAKRQFRIGDIAGEHTSFDKLFEGGRATYRGTAFGSDDAGGKLTYTIDF | 172 |
| | :*::.:* ..: .* :::.*::. : .* : .. ** :*.:*** | |

FIGURE 5C

| | |
|---|---|
| fHbpID59 | ASKQGHGKIEHLKTPEQNVELAAAELKADEKSHAVILGDTRYGSEEKGTYHLALFGDRAQ 239 |
| fHbpID31 | AAKQGHGKIEHLKTPEQNVELAAAELKADEKSHAVILGDTRYGSEEKGTYHLALFGDRAQ 239 |
| fHbpID79 | AAKQGHGKIEHLKTPEQNVELASAELKADEKSHAVILGDTRYGSEEKGTYHLALFGDRAQ 239 |
| fHbpID85 | AAKQGHGKIEHLKTPEQNVELASAELKADEKSHAVILGDTRYGSEEKGTYHLALFGDRAQ 239 |
| fHbpID72 | AAKQGHGKIEHLKTPEQNVELAAAELKADEKSHAVILGDTRYGSEEKGTYHLALFGDRAQ 237 |
| fHbpID84 | AAKQGHGKIEHLKTPEQNVELAAAELKADEKSHAVILGDTRYDSEEKGTYHLALFGDRAQ 239 |
| fHbpID70 | AAKQGHGKIEHLKTPEQNVELAAAELKADEKSHAVILGDTRYGSEEKGTYHLALFGDRAQ 239 |
| fHbpID46 | TKKQGYGGIEHLKTPEQNVELAAAELKADEKSHAVILGDTRYGSEEKGTYHLALFGDRAQ 239 |
| fHbpID99 | TKKQGYGRIEHLKTPEQNVELASAELKADEKSHAVILGDTRYGSEEKGTYHLALFGDRAQ 239 |
| fHbpID28 | TKKQGYGRIEHLKTLEQNVELAAAELKADEKSHAVILGDTRYGSEEKGTYHLALFGDRAQ 239 |
| fHbpID29 | TNKQGYGRIEHLKTPEQNVELAAAELKADEKSHAVILGDTRYGSEEKGTYHLALFGDRAQ 239 |
| fHbpID30 | TNKQGYGRIEHLKTPELNVDLASAELKADEKSHAVILGDTRYGSEEKGTYHLALFGDRAQ 236 |
| fHbpID64 | TNKQGYGRIEHLKTPELNVDLASAELKADEKSHAVILGDTRYGSEEKGTYHLALFGDRAQ 237 |
| fHbpID76 | TKKQGYGRIEHLKTPEQNVELASAELKADEKSHAVILGDTRYGSEEKGTYHLALFGDRAQ 238 |
| fHbpID45 | AAKQGHGKIEHLKTPEQNVELAAAELKADEKSHAVILGDTRYGSEEKGTYHLALFGDRAQ 238 |
| fHbpID47 | AAKQGHGKIEHLKSPELNVELATAELKADEKSHAVILGDTRYGSEEKGTYHLALFGDRAQ 234 |
| fHbpID82 | AAKQGHGKIEHLKSPELNVDLAAADIKPDGKRHAVISGSVLYNQAEKGSYSLGIFGGKAQ 234 |
| fHbpID1  | AAKQGNGKIEHLKSPELNVDLAAADIKPDGKRHAVISGSVLYNQAEKGSYSLGIFGGKAQ 232 |

FIGURE 5D

| | | |
|---|---|---|
| fHbpID59 | EIAGSATVKIGEKVHEIGIAGKQ | 262 |
| fHbpID31 | EIAGSATVKIGEKVHEIGIAGKQ | 262 |
| fHbpID79 | EIAGSATVKIGEKVHEIGIAGKQ | 262 |
| fHbpID85 | EIAGSATVKIREKVHEIGIAGKQ | 262 |
| fHbpID72 | EIAGSATVKIGEKVHEIGIAGKQ | 260 |
| fHbpID84 | EIAGSATVKIGEKVHEISIAGKQ | 262 |
| fHbpID70 | EIAGSATVKIGEKVHEIGIAGKQ | 262 |
| fHbpID46 | EIAGSATVKIGEKVHEIGIAGKQ | 262 |
| fHbpID99 | EIAGSATVKIGEKVHEIGIAGKQ | 262 |
| fHbpID28 | EIAGSATVKIGEKVHEIGIAGKQ | 262 |
| fHbpID29 | EIAGSATVKIGEKVHEIGIAGKQ | 262 |
| fHbpID30 | EIAGSATVKIGEKVHEIGIAGKQ | 262 |
| fHbpID64 | EIAGSATVKIGEKVHEIGIAGKQ | 259 |
| fHbpID76 | EIAGSATVKIREKVHEIGIAGKQ | 260 |
| fHbpID45 | EIAGSATVKIGEKVHEIGIAGKQ | 261 |
| fHbpID47 | EIAGSATVKIREKVHEISIAGKQ | 257 |
| fHbpID82 | EIAGSATVKIREKVHEIGIAGKQ | 257 |
| fHbpID1 | EVAGSAEVKTVNGIRHIGLAAKQ | 255 |
| | *:***:* *. :: .* *.*** | |

FIGURE 5E

SEQUENCE LISTING

```
<160> NUMBER OF SEQ ID NOS: 35

<210> SEQ ID NO 1
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45
```

```
Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
            195                 200                 205

Ser Gly Ser Val Leu Tyr Asn Gln Ala Glu Lys Gly Ser Tyr Ser Leu
210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 2
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 2

Val Asn Arg Thr Ala Phe Cys Cys Leu Ser Leu Thr Thr Ala Leu Ile
1               5                   10                  15

Leu Thr Ala

<210> SEQ ID NO 3
<211> LENGTH: 1231
<212> TYPE: PRT
<213> ORGANISM: Artificial sequence
<220> FEATURE:
<223> OTHER INFORMATION: Synthetic polypeptide

<400> SEQUENCE: 3

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
         50                  55                  60

Val Cys Arg Lys Gly Glu Trp Val Ala Leu Asn Pro Leu Arg Lys Cys
65                  70                  75                  80
```

-continued

```
Gln Lys Arg Pro Cys Gly His Pro Gly Asp Thr Pro Phe Gly Thr Phe
             85                  90                  95
Thr Leu Thr Gly Gly Asn Val Phe Glu Tyr Gly Val Lys Ala Val Tyr
        100                 105                 110
Thr Cys Asn Glu Gly Tyr Gln Leu Leu Gly Glu Ile Asn Tyr Arg Glu
        115                 120                 125
Cys Asp Thr Asp Gly Trp Thr Asn Asp Ile Pro Ile Cys Glu Val Val
    130                 135                 140
Lys Cys Leu Pro Val Thr Ala Pro Glu Asn Gly Lys Ile Val Ser Ser
145                 150                 155                 160
Ala Met Glu Pro Asp Arg Glu Tyr His Phe Gly Gln Ala Val Arg Phe
                165                 170                 175
Val Cys Asn Ser Gly Tyr Lys Ile Glu Gly Asp Glu Glu Met His Cys
            180                 185                 190
Ser Asp Asp Gly Phe Trp Ser Lys Glu Lys Pro Lys Cys Val Glu Ile
        195                 200                 205
Ser Cys Lys Ser Pro Asp Val Ile Asn Gly Ser Pro Ile Ser Gln Lys
    210                 215                 220
Ile Ile Tyr Lys Glu Asn Glu Arg Phe Gln Tyr Lys Cys Asn Met Gly
225                 230                 235                 240
Tyr Glu Tyr Ser Glu Arg Gly Asp Ala Val Cys Thr Glu Ser Gly Trp
                245                 250                 255
Arg Pro Leu Pro Ser Cys Glu Glu Lys Ser Cys Asp Asn Pro Tyr Ile
            260                 265                 270
Pro Asn Gly Asp Tyr Ser Pro Leu Arg Ile Lys His Arg Thr Gly Asp
        275                 280                 285
Glu Ile Thr Tyr Gln Cys Arg Asn Gly Phe Tyr Pro Ala Thr Arg Gly
    290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                325                 330                 335
His Glu Asn Met Arg Arg Pro Tyr Phe Pro Val Ala Val Gly Lys Tyr
            340                 345                 350
Tyr Ser Tyr Tyr Cys Asp Glu His Phe Glu Thr Pro Ser Gly Ser Tyr
        355                 360                 365
Trp Asp His Ile His Cys Thr Gln Asp Gly Trp Ser Pro Ala Val Pro
    370                 375                 380
Cys Leu Arg Lys Cys Tyr Phe Pro Tyr Leu Glu Asn Gly Tyr Asn Gln
385                 390                 395                 400
Asn His Gly Arg Lys Phe Val Gln Gly Lys Ser Ile Asp Val Ala Cys
                405                 410                 415
His Pro Gly Tyr Ala Leu Pro Lys Ala Gln Thr Thr Val Thr Cys Met
            420                 425                 430
Glu Asn Gly Trp Ser Pro Thr Pro Arg Cys Ile Arg Val Lys Thr Cys
        435                 440                 445
Ser Lys Ser Ser Ile Asp Ile Glu Asn Gly Phe Ile Ser Glu Ser Gln
    450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Arg Cys Gly Lys
                485                 490                 495
```

```
Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
            530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
        580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
        660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
        740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
        820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
        900                 905                 910
```

```
Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
930                 935                 940

Met Ser Asp Ser Tyr Gln Tyr Gly Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 4
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 4

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30
```

```
Asp Lys Gly Leu Lys Ser Leu Thr Leu Glu Asp Ser Ile Pro Gln Asn
         35                  40                  45

Gly Thr Leu Thr Leu Ser Ala Gln Gly Ala Glu Lys Thr Phe Lys Ala
 50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Pro Asn Gly Arg Leu His Tyr Ser
                165                 170                 175

Ile Asp Phe Thr Lys Lys Gln Gly Tyr Gly Arg Ile Glu His Leu Lys
                180                 185                 190

Thr Leu Glu Gln Asn Val Glu Leu Ala Ala Ala Glu Leu Lys Ala Asp
            195                 200                 205

Glu Lys Ser His Ala Val Ile Leu Gly Asp Thr Arg Tyr Gly Ser Glu
        210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 5
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 5

Cys Ser Ser Gly Gly Gly Gly Ser Gly Gly Gly Gly Val Ala Ala Asp
1               5                  10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
 50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125
```

```
Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Gly Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```

<210> SEQ ID NO 6
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 6

```
Cys Ser Ser Gly Gly Gly Gly Ser Gly Gly Ile Ala Ala Asp Ile Gly
1               5                   10                  15

Thr Gly Leu Ala Asp Ala Leu Thr Ala Pro Leu Asp His Lys Asp Lys
            20                  25                  30

Gly Leu Lys Ser Leu Thr Leu Glu Asp Ser Ile Pro Gln Asn Gly Thr
        35                  40                  45

Leu Thr Leu Ser Ala Gln Gly Ala Glu Lys Thr Phe Lys Ala Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Gly Gly Lys Ala Glu Tyr His Gly Lys
145                 150                 155                 160

Ala Phe Ser Ser Asp Asp Pro Asn Gly Arg Leu His Tyr Ser Ile Asp
                165                 170                 175

Phe Thr Lys Lys Gln Gly Tyr Gly Arg Ile Glu His Leu Lys Thr Pro
            180                 185                 190

Glu Gln Asn Val Glu Leu Ala Ser Ala Glu Leu Lys Ala Asp Glu Lys
        195                 200                 205

Ser His Ala Val Ile Leu Gly Asp Thr Arg Tyr Gly Ser Glu Glu Lys
    210                 215                 220
```

```
Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
            245                 250                 255

Ala Gly Lys Gln
        260

<210> SEQ ID NO 7
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 7

Cys Ser Ser Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Gly Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 8
<211> LENGTH: 262
<212> TYPE: PRT
<213> ORGANISM: Artificial sequence
<220> FEATURE:
<223> OTHER INFORMATION: Synthetic polypeptide
```

```
<400> SEQUENCE: 8

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 9
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 9

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80
```

-continued

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Ser Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 10
<211> LENGTH: 259
<212> TYPE: PRT
<213> ORGANISM: Artificial sequence
<220> FEATURE:
<223> OTHER INFORMATION: Synthetic polypeptide

<400> SEQUENCE: 10

Cys Ser Ser Gly Ser Gly Gly Gly Val Ala Ala Asp Ile Gly
1               5                   10                  15

Gly Leu Ala Asp Ala Leu Thr Ala Pro Leu Asp His Lys Asp Lys Gly
            20                  25                  30

Leu Lys Ser Leu Thr Leu Glu Asp Ser Ile Pro Gln Asn Gly Thr Leu
        35                  40                  45

Thr Leu Ser Ala Gln Gly Ala Glu Lys Thr Phe Lys Ala Gly Asp Lys
    50                  55                  60

Asp Asn Ser Leu Asn Thr Gly Lys Leu Lys Asn Asp Lys Ile Ser Arg
65                  70                  75                  80

Phe Asp Phe Val Gln Lys Ile Glu Val Asp Gly Gln Thr Ile Thr Leu
                85                  90                  95

Ala Ser Gly Glu Phe Gln Ile Tyr Lys Gln Asn His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Gly Gly Lys Ala Glu Tyr His Gly Lys Ala
145                 150                 155                 160

Phe Ser Ser Asp Pro Asn Gly Arg Leu His Tyr Thr Ile Asp Phe
                165                 170                 175

```
Thr Asn Lys Gln Gly Tyr Gly Arg Ile Glu His Leu Lys Thr Pro Glu
                180                 185                 190

Leu Asn Val Asp Leu Ala Ser Ala Glu Leu Lys Ala Asp Glu Lys Ser
            195                 200                 205

His Ala Val Ile Leu Gly Asp Thr Arg Tyr Gly Ser Glu Glu Lys Gly
        210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln

<210> SEQ ID NO 11
<211> LENGTH: 261
<212> TYPE: PRT
<213> ORGANISM: Artificial sequence
<220> FEATURE:
<223> OTHER INFORMATION: Synthetic polypeptide

<400> SEQUENCE: 11

Cys Ser Ser Gly Ser Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260
```

<210> SEQ ID NO 12
<211> LENGTH: 257
<212> TYPE: PRT
<213> ORGANISM: Artificial sequence
<220> FEATURE:
<223> OTHER INFORMATION: Synthetic polypeptide

<400> SEQUENCE: 12

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Lys
                20                  25                  30

Ser Leu Thr Leu Glu Asp Ser Ile Ser Gln Asn Gly Thr Leu Thr Leu
            35                  40                  45

Ser Ala Gln Gly Ala Glu Lys Thr Phe Lys Val Gly Asp Lys Asp Asn
        50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asn His Ser Ala Val Val Ala Leu
            100                 105                 110

Gln Ile Glu Lys Ile Asn Asn Pro Asp Lys Ile Asp Ser Leu Ile Asn
        115                 120                 125

Gln Arg Ser Phe Leu Val Ser Gly Leu Gly Gly Glu His Thr Ala Phe
    130                 135                 140

Asn Gln Leu Pro Gly Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ala Ala Glu Leu Lys Ala Asp Glu Lys Ser His Ala
        195                 200                 205

Val Ile Leu Gly Asp Thr Arg Tyr Gly Ser Glu Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Ser Ile Ala Gly Lys
                245                 250                 255

Gln
```

<210> SEQ ID NO 13
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 13

```
Cys Ser Ser Gly Gly Gly Ser Gly Ser Gly Gly Val Ala Ala Asp
1               5                   10                  15

Ile Gly Thr Gly Leu Ala Asp Ala Leu Thr Thr Pro Leu Asp His Lys
                20                  25                  30

Asp Lys Gly Leu Lys Ser Leu Thr Leu Glu Asp Ser Ile Pro Gln Asn
            35                  40                  45
```

```
Gly Thr Leu Thr Leu Ser Ala Gln Gly Ala Glu Lys Thr Phe Lys Ala
     50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asp His Ser
                100                 105                 110

Ala Val Val Ala Leu Gln Ile Glu Lys Ile Asn Asn Pro Asp Lys Ile
            115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
                180                 185                 190

Thr Pro Glu Gln Asn Val Glu Leu Ala Ser Ala Glu Leu Lys Ala Asp
                195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
                260

<210> SEQ ID NO 14
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 14

Cys Ser Ser Gly Gly Gly Gly Ser Gly Gly Gly Gly Val Ala Ala Asp
 1               5                  10                  15

Ile Gly Thr Gly Leu Ala Asp Ala Leu Thr Ala Pro Leu Asp His Lys
                 20                  25                  30

Asp Lys Gly Leu Lys Ser Leu Thr Leu Glu Asp Ser Ile Pro Gln Asn
             35                  40                  45

Gly Thr Leu Thr Leu Ser Ala Gln Gly Ala Glu Lys Thr Phe Lys Ala
     50                  55                  60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asp His Ser
                100                 105                 110

Ala Val Val Ala Leu Gln Ile Glu Lys Ile Asn Asn Pro Asp Lys Ile
            115                 120                 125

Asp Ser Leu Ile Asn Gln Arg Ser Phe Leu Val Ser Gly Leu Gly Gly
130                 135                 140
```

```
Glu His Thr Ala Phe Asn Gln Leu Pro Gly Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Ala Glu Leu Lys Ala Asp
        195                 200                 205

Glu Lys Ser His Ala Val Ile Leu Gly Asp Thr Arg Tyr Asp Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Ser Ile Ala Gly Lys Gln
            260
```

<210> SEQ ID NO 15
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 15

```
Cys Ser Ser Gly Gly Gly Ser Gly Ser Gly Gly Val Ala Ala Asp
1               5                   10                  15

Ile Gly Thr Gly Leu Ala Asp Ala Leu Thr Thr Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ser Lys Gln Gly His Gly Lys Ile Glu His Leu Lys
            180                 185                 190

Thr Pro Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240
```

Ile Ala Gly Ser Ala Thr Val Lys Ile Gly Glu Lys Val His Glu Ile
                245                 250                 255

Gly Ile Ala Gly Lys Gln
            260

<210> SEQ ID NO 16
<211> LENGTH: 257
<212> TYPE: PRT
<213> ORGANISM: Artificial sequence
<220> FEATURE:
<223> OTHER INFORMATION: Synthetic polypeptide

<400> SEQUENCE: 16

Cys Ser Ser Gly Gly Gly Val Ala Ala Asp Ile Gly Thr Gly Leu
1               5                   10                  15

Ala Asp Ala Leu Thr Ala Pro Leu Asp His Lys Asp Lys Gly Leu Lys
                20                  25                  30

Ser Leu Thr Leu Glu Asp Ser Ile Pro Gln Asn Gly Thr Leu Thr Leu
            35                  40                  45

Ser Ala Gln Gly Ala Glu Lys Thr Phe Lys Ala Gly Asp Lys Asp Asn
        50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asn His Ser Ala Val Val Ala Leu
                100                 105                 110

Gln Ile Glu Lys Ile Asn Asn Pro Asp Lys Ile Asp Ser Leu Ile Asn
            115                 120                 125

Gln Arg Ser Phe Leu Val Ser Gly Leu Gly Gly Glu His Thr Ala Phe
        130                 135                 140

Asn Gln Leu Pro Val Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Ser Pro Glu Leu Asn
                180                 185                 190

Val Glu Leu Ala Thr Ala Glu Leu Lys Ala Asp Glu Lys Ser His Ala
            195                 200                 205

Val Ile Leu Gly Asp Thr Arg Tyr Gly Ser Glu Glu Lys Gly Thr Tyr
        210                 215                 220

His Leu Ala Leu Phe Gly Asp Arg Ala Gln Glu Ile Ala Gly Ser Ala
225                 230                 235                 240

Thr Val Lys Ile Arg Glu Lys Val His Glu Ile Gly Ile Ala Gly Lys
                245                 250                 255

Gln

<210> SEQ ID NO 17
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 17

```
Cys Ser Ser Gly Gly Gly Gly Ser Gly Gly Val Ala Ala Asp
  1               5                  10                  15

Ile Gly Thr Gly Leu Ala Asp Ala Leu Thr Thr Pro Leu Asp His Lys
                 20                  25                  30

Asp Lys Gly Leu Lys Ser Leu Thr Leu Glu Asp Ser Ile Pro Gln Asn
             35                  40                  45

Gly Thr Leu Thr Leu Ser Ala Gln Gly Ala Glu Lys Thr Phe Lys Ala
 50                  55                      60

Gly Asp Lys Asp Asn Ser Leu Asn Thr Gly Lys Leu Lys Asn Asp Lys
 65                  70                  75                  80

Ile Ser Arg Phe Asp Phe Val Gln Lys Ile Glu Val Asp Gly Gln Thr
                 85                  90                  95

Ile Thr Leu Ala Ser Gly Glu Phe Gln Ile Tyr Lys Gln Asp His Ser
                100                 105                 110

Ala Val Val Ala Leu Gln Ile Glu Lys Ile Asn Asn Pro Asp Lys Ile
             115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
                180                 185                 190

Thr Pro Glu Gln Asn Val Glu Leu Ala Ala Ala Glu Leu Lys Ala Asp
            195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```

<210> SEQ ID NO 18
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 18

```
Cys Ser Ser Gly Gly Gly Gly Ser Gly Gly Val Ala Ala Asp
  1               5                  10                  15

Ile Gly Thr Gly Leu Ala Asp Ala Leu Thr Thr Pro Leu Asp His Lys
                 20                  25                  30

Asp Lys Gly Leu Lys Ser Leu Thr Leu Glu Asp Ser Ile Pro Gln Asn
             35                  40                  45

Gly Thr Leu Thr Leu Ser Ala Gln Gly Ala Glu Lys Thr Phe Lys Ala
 50                  55                      60

Gly Asp Lys Asp Asn Ser Leu Asn Thr Gly Lys Leu Lys Asn Asp Lys
 65                  70                  75                  80
```

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Ser Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Arg Glu Lys Val His Glu Ile
                245                 250                 255

Gly Ile Ala Gly Lys Gln
            260

<210> SEQ ID NO 19
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 19

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
        180                 185                 190

Thr Pro Glu Gln Asn Val Glu Leu Ala Ala Ala Glu Leu Lys Ala Asp
            195                 200                 205

Glu Lys Ser His Ala Val Ile Leu Gly Asp Thr Arg Tyr Gly Ser Glu
        210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
            245                 250                 255

Gly Ile Ala Gly Lys Gln
            260

<210> SEQ ID NO 20
<211> LENGTH: 260
<212> TYPE: PRT
<213> ORGANISM: Artificial sequence
<220> FEATURE:
<223> OTHER INFORMATION: Synthetic polypeptide

<400> SEQUENCE: 20

Cys Ser Ser Gly Gly Gly Ser Gly Gly Val Ala Ala Asp Ile Gly
1               5                   10                  15

Thr Gly Leu Ala Asp Ala Leu Thr Thr Pro Leu Asp His Lys Asp Lys
            20                  25                  30

Gly Leu Lys Ser Leu Thr Leu Glu Asp Ser Ile Pro Gln Asn Gly Thr
        35                  40                  45

Leu Thr Leu Ser Ala Gln Gly Ala Glu Lys Thr Phe Lys Ala Gly Asp
    50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Gly Gly Lys Ala Glu Tyr His Gly Lys
145                 150                 155                 160

Ala Phe Ser Ser Asp Asp Ala Gly Gly Lys Leu Thr Tyr Thr Ile Asp
                165                 170                 175

Phe Ala Ala Lys Gln Gly His Gly Lys Ile Glu His Leu Lys Thr Pro
            180                 185                 190

Glu Gln Asn Val Glu Leu Ala Ala Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Gly Glu Lys Val His Glu Ile Gly Ile
                245                 250                 255

Ala Gly Lys Gln
            260

```
<210> SEQ ID NO 21
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 21

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Ser Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Gly Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Arg Glu Lys Val His Glu Ile
                245                 250                 255

Gly Ile Ala Gly Lys Gln
            260

<210> SEQ ID NO 22
<211> LENGTH: 262
<212> TYPE: PRT
<213> ORGANISM: Artificial sequence
<220> FEATURE:
<223> OTHER INFORMATION: Synthetic polypeptide

<400> SEQUENCE: 22

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45
```

Gly Thr Leu Thr Leu Ser Ala Gln Gly Ala Glu Arg Thr Phe Lys Ala
             50                  55                  60
Gly Asp Lys Asp Asn Ser Leu Asn Thr Gly Lys Leu Lys Asn Asp Lys
 65                  70                  75                  80
Ile Ser Arg Phe Asp Phe Ile Arg Gln Ile Glu Val Asp Gly Gln Leu
                 85                  90                  95
Ile Thr Leu Glu Ser Gly Glu Phe Gln Ile Tyr Lys Gln Asp His Ser
                100                 105                 110
Ala Val Ala Leu Gln Ile Glu Lys Ile Asn Asn Pro Asp Lys Ile
            115                 120                 125
Asp Ser Leu Ile Asn Gln Arg Ser Phe Leu Val Ser Gly Leu Gly Gly
130                 135                 140
Glu His Thr Ala Phe Asn Gln Leu Pro Asp Gly Lys Ala Glu Tyr His
145                 150                 155                 160
Gly Lys Ala Phe Ser Ser Asp Ala Gly Gly Lys Leu Thr Tyr Thr
                165                 170                 175
Ile Asp Phe Ala Ala Lys Gln Gly His Gly Lys Ile Glu His Leu Lys
                180                 185                 190
Thr Pro Glu Gln Asn Val Glu Leu Ala Ala Ala Glu Leu Lys Ala Asp
                195                 200                 205
Glu Lys Ser His Ala Val Ile Leu Gly Asp Thr Arg Tyr Gly Ser Glu
210                 215                 220
Glu Lys Gly Thr Tyr His Leu Ala Leu Phe Gly Asp Arg Ala Gln Glu
225                 230                 235                 240
Ile Ala Gly Ser Ala Thr Val Lys Ile Gly Glu Lys Val His Glu Ile
                245                 250                 255
Gly Ile Ala Gly Lys Gln
                260

<210> SEQ ID NO 23
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 23

Cys Ser Ser Gly Gly Gly Gly Val Ala Ala Asp Ile Gly Ala Gly Leu
  1               5                  10                  15
Ala Asp Ala Leu Thr Ala Pro Leu Asp His Lys Asp Lys Gly Leu Gln
                 20                  25                  30
Ser Leu Thr Leu Asp Gln Ser Val Arg Lys Asn Glu Lys Leu Lys Leu
             35                  40                  45
Ala Ala Gln Gly Ala Glu Lys Thr Tyr Gly Asn Gly Asp Ser Leu Asn
         50                  55                  60
Thr Gly Lys Leu Lys Asn Asp Lys Val Ser Arg Phe Asp Phe Ile Arg
 65                  70                  75                  80
Gln Ile Glu Val Asp Gly Gln Leu Ile Thr Leu Glu Ser Gly Glu Phe
                 85                  90                  95
Gln Val Tyr Lys Gln Ser His Ser Ala Leu Thr Ala Phe Gln Thr Glu
                100                 105                 110
Gln Ile Gln Asp Ser Glu His Ser Gly Lys Met Val Ala Lys Arg Gln
            115                 120                 125
Phe Arg Ile Gly Asp Ile Ala Gly Glu His Thr Ala Phe Asn Gln Leu
        130                 135                 140

```
Pro Gly Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 24
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 24

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Ser Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ala Phe Asn Gln Leu
        130                 135                 140

Pro Gly Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

```
<210> SEQ ID NO 25
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 25

Phe Leu Leu Ala Val
1               5

<210> SEQ ID NO 26
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 26

Gly Gly Ser Gly
1

<210> SEQ ID NO 27
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 27

Gly Gly Ser Gly Gly
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 28

Gly Ser Gly Ser Gly
1               5

<210> SEQ ID NO 29
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 29

Gly Ser Gly Gly Gly
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 30

Gly Gly Gly Ser Gly
1               5
```

```
<210> SEQ ID NO 31
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 31

Gly Ser Ser Ser Gly
1               5

<210> SEQ ID NO 32
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 32

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 33
<211> LENGTH: 5
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MISC_FEATURE
<222> LOCATION: (5)..(5)
<223> OTHER INFORMATION: This residue is repeated at least once.

<400> SEQUENCE: 33

Gly Ser Gly Gly Ser
1               5

<210> SEQ ID NO 34
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: This residue is repeated at least once.

<400> SEQUENCE: 34

Gly Gly Gly Ser
1

<210> SEQ ID NO 35
<211> LENGTH: 5
<212> TYPE: PRT
<213> ORGANISM: Artificial Sequence
<220> FEATURE:
<223> OTHER INFORMATION: Synthetic sequence

<400> SEQUENCE: 35

Thr Tyr His Leu Ala
1               5
```

NON-NATURALLY OCCURRING FACTOR H BINDING PROTEINS (FHBP) AND METHODS OF USE THEREOF

CROSS REFERENCE TO RELATED APPLICATIONS

This application claims priority benefit of U.S. Provisional Patent Application Ser. No. 61/861,662, Filed on Aug. 2, 2013, the disclosure of which application is herein incorporated by reference in its entirety.

STATEMENT REGARDING FEDERALLY SPONSORED RESEARCH

This invention was made with government support under grant no. R01 AI 099125-01 awarded by the National Institute of Allergy and Infectious Diseases, National Institutes of Health. The government has certain rights in this invention.

INTRODUCTION

*Neisseria meningitidis* (*N. meningitidis*) is a Gram-negative bacterium which colonizes the human upper respiratory tract and is responsible for worldwide sporadic and cyclical epidemic outbreaks of, most notably, meningitis and sepsis. Infection and morbidity rates are highest in children under 2 years of age. Like other Gram-negative bacteria, *N. meningitidis* typically possess a cytoplasmic membrane, a peptidoglycan layer, an outer membrane which together with the capsular polysaccharide constitute the bacterial wall, and pili, which project into the outside environment. Encapsulated strains of *N. meningitidis* are a major cause of bacterial meningitis and septicemia in children and young adults. The prevalence of invasive *N. meningitidis* infections have driven the search for effective vaccines that can confer immunity across different strains, and particularly across genetically diverse group B strains with different serotypes or serosubtypes.

Factor H Binding Protein (fHbp, also referred to in the art as lipoprotein 2086 (Fletcher et al (2004) *Infect Immun* 72:2088-2100), Genome-derived Neisserial antigen (GNA) 1870 (Masignani et al. (2003) *J Exp Med* 197:789-99) or "741") is a surface-exposed lipoprotein expressed in the *N. meningitidis* bacterium. fHbp binds to human complement factor H (fH), which down-regulates complement activation. Binding of fH to the bacterial surface is an important mechanism by which the pathogen survives in non-immune human serum or blood and evades innate host defenses. Recently, genetic variation in the human factor H gene cluster was found to affect susceptibility to developing meningococcal disease (Davila S et al. (2010) Nat Genetics doi:10.1038/ng.640). Binding of fH to fHbp is specific for human fH and could account for why *Neisseria meningitidis* is strictly a human pathogen.

There remains a need for a fHbp polypeptide that can elicit effective bactericidal antibody responses.

SUMMARY

Non-naturally occurring factor H binding proteins derived from variant 3 fHbp that can elicit antibodies that are bactericidal for at least one strain of *N. meningitidis*, and methods of use of such proteins, are provided.

In certain embodiments, a non-naturally occurring factor H binding protein (fHbp) derived from a naturally occurring variant 3 fHbp is disclosed. The non-naturally fHbp may include a substitution of the histidine at position 223 of the naturally occurring variant 3 fHbp with an amino acid selected from the group consisting of arginine, lysine, phenylalanine, tyrosine, or tryptophan, wherein the numbering of position 223 is based on the numbering of the mature fHbp ID 1. The non-naturally occurring fHbp may have a lower affinity for human factor H (fH) than fHbp ID 79.

In certain embodiments, the histidine may be substituted with arginine.

In certain cases, the variant 3 fHbp may be a modular group V fHbp. In other cases, the variant 3 fHbp may be a modular group II fHbp.

Exemplary non-naturally occurring fHbp may include an amino acid sequence having at least 90% sequence identity to the amino acid sequence of the fHbp ID 79.

In certain cases, the non-naturally occurring fHbp may include the amino acid sequence of fHbp ID 28 with the amino acid substitution H223R.

In certain cases, the non-naturally occurring fHbp may include the amino acid sequence of fHbp ID 67 with the amino acid substitution H223R.

In certain cases, the non-naturally occurring fHbp may include the amino acid sequence of fHbp ID 175 with the amino acid substitution H223R.

In certain cases, the non-naturally occurring fHbp may include the amino acid sequence of fHbp ID 79 with the amino acid substitution H223R.

In certain cases, the non-naturally occurring fHbp may include the amino acid sequence of fHbp ID 45 with the amino acid substitution H223R.

In another embodiment, an immunogenic composition is provided. The immunogenic composition may include: a) the non-naturally occurring fHbp as disclosed herein; and b) a pharmaceutically acceptable excipient.

In certain cases, the non-naturally occurring fHbp may be expressed on surface of a vesicle preparation prepared from a *N. meningitidis* strain expressing the non-naturally occurring fHbp.

In certain cases, the non-naturally occurring fHbp may be present as an isolated polypeptide in the immunogenic composition.

In exemplary cases, pharmaceutically acceptable excipient may include an adjuvant.

In certain cases, the immunogenic composition may further include an additional *N. meningitidis* antigen.

A method of eliciting an antibody response in a mammal against *N. meningitidis* is provided. The method may involve administering to a mammal the non-naturally occurring fHbp disclosed herein, or the immunogenic composition as provided herein.

In certain cases, the administering provides for production of antibodies that are bactericidal against *N. meningitidis*.

A nucleic acid encoding the non-naturally occurring fHbp provided herein is also disclosed. Also provided herein is a recombinant expression vector that includes the nucleic acid encoding the non-naturally occurring fHbp. Exemplary embodiments include a genetically modified host cell that includes the nucleic acid encoding the non-naturally occurring fHbp or the recombinant expression vector that includes the nucleic acid encoding the non-naturally occurring fHbp.

Another immunogenic composition is disclosed herein. This immunogenic composition may include: a) a vesicle obtained from a genetically modified *Neisseria* host cell that is genetically modified with a nucleic acid encoding the non-naturally occurring fHbp according to the present disclosure, such that the encoded non-naturally occurring fHbp is produced by the genetically modified host cell, wherein the vesicle includes the encoded non-naturally occurring fHbp; and b) a pharmaceutically acceptable excipient.

In certain cases, the vesicle may be a native outer membrane vesicle.

In certain cases, the host cell may be genetically modified to provide for decreased or no activity of a polypeptide product of the lpxL1 gene and/or the lpxL2 gene.

In exemplary embodiments, the host cell is genetically modified to provide for increased expression of a Neisserial antigen.

A method of eliciting an antibody response against *Neisseria* in a mammal is provided. The method may include administering to a mammal the immunogenic composition that includes: a) a vesicle obtained from a genetically modified *Neisseria* host cell that is genetically modified with a nucleic acid encoding the non-naturally occurring fHbp according to the present disclosure, such that the encoded non-naturally occurring fHbp is produced by the genetically modified host cell, wherein the vesicle includes the encoded non-naturally occurring fHbp; and b) a pharmaceutically acceptable excipient.

BRIEF DESCRIPTION OF THE DRAWINGS

FIG. 4. An alignment of amino acid sequence of mature fHbp ID1 (SEQ ID NO:1), fHbp ID 22 (SEQ ID NO:32), fHbp ID 79 (SEQ ID NO:13), and fHbp ID 28 (SEQ ID NO:4). H223 is indicated with an arrow.

FIGS. 5A-5E. An alignment of amino acid sequence of mature v. 3 fHbps (fHbpID59, SEQ ID NO:15; fHbpID31, SEQ ID NO:17; fHbpID79, SEQ ID NO:13; fHbpID85, SEQ ID NO:18; fHbpID72, SEQ ID NO:20; fHbpID84, SEQ ID NO:14; fHbpID70, SEQ ID NO:19; fHbpID46, SEQ ID NO:5; fHbpID99, SEQ ID NO:8; fHbpID28, SEQ ID NO:4; fHbpID29, SEQ ID NO:7; fHbpID30, SEQ ID NO:9; fHbpID64, SEQ ID NO:10; fHbpID76, SEQ ID NO:6; fHbpID45, SEQ ID NO:11; fHbpID47, SEQ ID NO:12; fHbpID82, SEQ ID NO:16) and mature v. 1 fHbpID1 (SEQ ID NO:1). H223 is indicated with an arrow.

Figure 1:
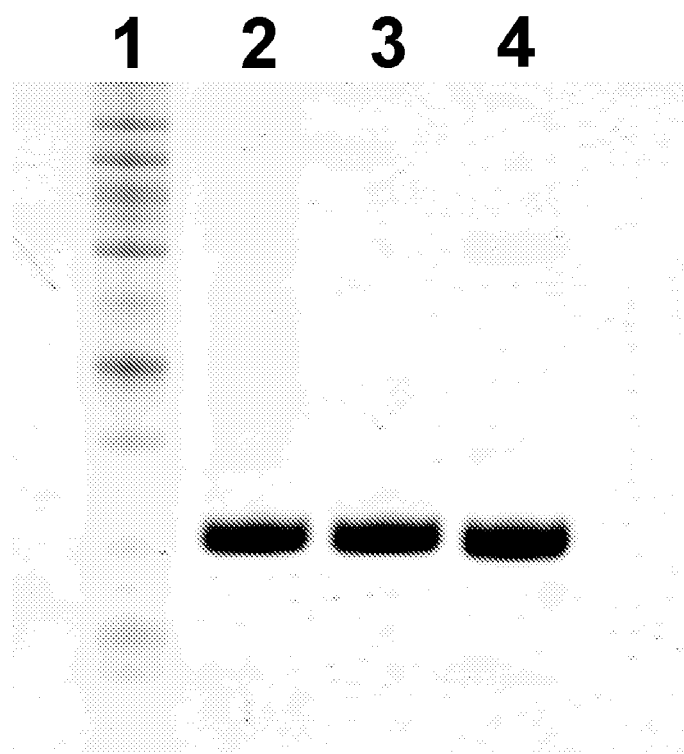
FIG. 1. SDS-polyacrylamide gel indicating size and purity of recombinant fHbp ID 79 wild-type and mutants. Lane 1, Benchmark Ladder (Invitrogen); lane 2 fHbp ID 79 wild-type; lane 3 fHbp ID 79 H223R mutant; lane 4, fHbp ID 79 H223A mutant. 2 µg of each of the recombinant fHbps was loaded on the gel. Note that the amino acid numbering is based on the numbering of the mature fHbp ID 1. See Example 1 for details.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to amino acid modifications, including amino acid substitutions, relative to a reference amino acid sequence are specifically embraced by the present invention and are disclosed herein just as if each and every combination were individually and explicitly disclosed, to the extent that such combinations embrace polypeptides having desired features, e.g., non-naturally occurring fHbp polypeptides having a lower affinity for a human fH than that of a naturally occurring fHbp. In addition, all sub-combinations of such amino acid modifications (including amino acid substitutions) listed in the embodiments describing such amino acid modifications are also specifically embraced by the present invention and are disclosed herein just as if each and every such sub-combination of such amino acid modifications was individually and explicitly disclosed herein.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As noted above, non-naturally occurring factor H binding proteins derived from variant 3 fHbp that can elicit antibodies that are bactericidal for at least one strain of *N. meningitidis*, and methods of use such proteins, are provided.

Definitions

"Factor H Binding Protein" (fHbp), which is also known in the literature as GNA1870, GNA 1870, ORF2086, LP2086 (lipoprotein 2086), and "741" refers to a class of *N. meningitidis* polypeptides. fHbp is found in nature as a lipoprotein expressed on the surface of *N. meningitidis* strains. fHbps have been sub-divided into three fHbp variant groups (referred to as variant 1 (v.1), variant 2 (v.2), and variant 3 (v.3) in some reports (Masignani et al. (2003) *J Exp Med* 197:789-99) and Family A and B in other reports (see, e.g., Fletcher et al. (2004) *Infect Immun* 72:2088-2100)) based on amino acid sequence variability and immunologic cross-reactivity (Masignani et al. (2003) *J Exp Med* 197: 789-99). Each unique fHbp found in *N. meningitidis* is also assigned a fHbp peptide ID according to neisseria.org or pubmlst.org/neisseria/fHbp/ website. Because the length of variant 2 (v.2) fHbp protein (from strain 8047, fHbp ID 77) and variant 3 (v.3) fHBP (from strain M1239, fHbp ID 28) differ by −1 and +7 amino acid residues, respectively, from that of MC58 (fHbp ID 1), the numbering used to refer to residues for v.2 and v.3 fHbp proteins differs from numbering based on the actual amino acid sequences of these proteins.

The term "heterologous" or "chimeric" refers to two components that are defined by structures derived from different sources or progenitor sequences. For example, where "heterologous" is used in the context of a chimeric polypeptide, the chimeric polypeptide can include operably linked amino acid sequences that can be derived from different polypeptides of different phylogenic groupings (e.g., a first component from an α and a second component from a β progenitor amino acid sequences). A chimeric polypeptide containing two or more defined segments, each of which is from a different progenitor, can be naturally-occurring or man-made (non-naturally-occurring). See Beernink P T, Granoff D M (2009) *Microbiology* 155:2873-83 for more detail on naturally-occurring chimeras. Non-naturally occurring chimeras refers to "man-made chimeras" and encompass fHbp with heterologous components that are not found in nature.

A "heterologous" or "chimeric" polypeptide may also contain two or more different components, each derived from a different fHbp (e.g. variant 1, 2, or 3). The component may be operably linked at any position along the length of the fHbp polypeptide.

"Heterologous" in the context of a polynucleotide encoding any chimeric polypeptide as described above can include operably linked nucleic acid sequence that can be derived from different genes (e.g., a first component from a nucleic acid encoding a fHBP v.1 polypeptide and a second component from a nucleic acid encoding a fHBP v.2 polypeptide) or different progenitor amino acid sequences (α or β).

Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding an fHbp polypeptide or domain thereof is said to be a heterologous nucleic acid.

"Heterologous" in the context of recombinant cells can refer to the presence of a nucleic acid (or gene product, such as a polypeptide) that is of a different genetic origin than the host cell in which it is present. For example, a Neisserial amino acid or nucleic acid sequence of one strain is heterologous to a Neisserial host of another strain.

"Derived from" in the context of an amino acid sequence or polynucleotide sequence (e.g., an amino acid sequence "derived from" fHbp variant 3, e.g., fHbp ID 79) is meant to indicate that the polypeptide or nucleic acid has a sequence that is based on that of a reference polypeptide or nucleic acid (e.g., a naturally occurring fHbp protein or encoding nucleic acid), and is not meant to be limiting as to the source or method in which the protein or nucleic acid is made. Non-limiting examples of reference polypeptides and reference polynucleotides from which an amino acid sequence or polynucleotide sequence may be "derived from" include a naturally-occurring fHbp, e.g., fHbp ID 79, and a non-naturally-occurring fHbp. "Derived from" in the context of bacterial strains is meant to indicate that a strain was obtained through passage in vivo, or in in vitro culture, of a parental strain and/or is a recombinant cell obtained by modification of a parental strain.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Guidance for such substitutions can be drawn from alignments of amino acid sequences of polypeptides presenting the epitope of interest.

The term "protective immunity" means that a vaccine or immunization schedule that is administered to a mammal induces an immune response that prevents, retards the development of, or reduces the severity of a disease that is caused by *N. meningitidis*, or diminishes or altogether eliminates the symptoms of the disease. Protective immunity can be accompanied by production of bactericidal antibodies. It should be noted that production of bactericidal antibodies against *N. meningitidis* is accepted in the field as predictive of a vaccine's protective effect in humans. (Goldschneider et al. (1969) *J. Exp. Med.* 129:1307; Borrow et al. (2001) *Infect Immun.* 69:1568).

The phrase "a disease caused by a strain of *Neisseria meningitidis*" encompasses any clinical symptom or combination of clinical symptoms that are present in an infection of a human with a *N. meningitidis*. These symptoms include but are not limited to: colonization of the upper respiratory tract (e.g., mucosa of the nasopharynx and tonsils) by a pathogenic strain of *N. meningitidis*, penetration of the bacteria into the mucosa and the submucosal vascular bed, septicemia, septic shock, inflammation, haemorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "specifically binds to an antibody" or "specifically immunoreactive with", in the context of an antigen (e.g., a polypeptide antigen) refers to a binding reaction which is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and do not bind in a significant amount to other epitopes present in the antigen and/or in the sample.

The phrase "in a sufficient amount to elicit an immune response" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchterlony immunodiffusion; binding detection assays of, for example, spot, Western blot or antigen arrays; cytotoxicity assays, etc.

A "surface antigen" is an antigen that is present in a surface structure of N. meningitidis (e.g. the outer membrane, capsule, pili, etc.).

"Isolated" refers to a molecule of interest that is in an environment different from that in which the molecule may naturally occur. "Isolated" is meant to include compounds/polypeptides that are within samples that are substantially enriched for the compound/polypeptides of interest and/or in which the compound/polypeptides of interest is partially or substantially purified.

"Enriched" means that a sample is non-naturally manipulated (e.g., by a scientist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, polypeptide, and the like).

A "knock-out" or "knockout" in the context of a target gene refers to an alteration in the sequence of the gene that results in a decrease of function of the target gene, e.g., such that target gene expression is undetectable or insignificant, and/or the gene product is not functional or not significantly functional. For example, a "knockout" of a gene involved in lipopolysaccharide (LPS) synthesis indicates that function of the gene has been substantially decreased so that the expression of the gene is not detectable or is only present at insignificant levels and/or a biological activity of the gene product (e.g., an enzymatic activity) is significantly reduced relative to prior to the modification or is not detectable. "Knock-outs" encompass conditional knock-outs, where alteration of the target gene can occur upon, for example, exposure to a predefined set of conditions (e.g., temperature, osmolarity, exposure to substance that promotes target gene alteration, and the like). A "knock-in" or "knockin" of a target gene refers to a genetic alteration in a gene that that results in an increase in a function provided by the target gene.

Non-Naturally Occurring FHBP Polypeptides

Before describing further fHbps contemplated by the present disclosure, it is helpful to describe some naturally-occurring fHbps. Unique naturally-occurring fHbps found in *N. meningitidis* are each assigned a fHbp peptide ID according to neisseria.org and pubmlst.org/neisseria/fHbp websites. This convention of naming fHbps will be adopted throughout the present disclosure.

For convenience and clarity, the native amino acid sequence of fHbp ID 1 (v.1 fHbp of the *N. meningitidis* strain MC58) is selected as a reference sequence for describing amino acid position in all naturally occurring and non-naturally occurring fHbp amino acid sequences, encompassing chimeric and/or mutants of fHbps described herein. The amino acid sequence of fHbp ID 1 is presented below: fHbp ID1 (v. 1)

(SEQ ID NO: 1)

```
CSSGGGGVAADIGAGLADALTAPLDHKDKGLQSLTLDQSVRKNEKLKLAA

QGAEKTYGNGDSLNTGKLKNDKVSRFDFIRQIEVDGQLITLESGEFQVYK

QSHSALTAFQTEQIQDSEHSGKMVAKRQFRIGDIAGEHTSFDKLPEGGRA

TYRGTAFGSDDAGGKLTYTIDFAAKQGNGKIEHLKSPELNVDLAAADIKP

DGKRHAVISGSVLYNQAEKGSYSLGIFGGKAQEVAGSAEVKTVNGIRHIG

LAAKQ.
```

In referring to an amino acid residue position in a fHbp, the position number used herein corresponds to the amino acid residue number of fHbp ID 1.

See FIG. 4 for an alignment of various fHbps and the amino acid residues in each fHbp corresponding to those of fHbp ID 1. As seen in FIG. 4 and SEQ ID NO: 1, position number 1 refers to the first amino acid residue shown in fHbp ID 1, which is a cysteine. The fHbp referred to herein may sometimes contain an additional leader sequence at the N-terminus. For example, fHbp ID 1 may have a leader sequence of (SEQ ID NO: 2)

VNRTAFCCLSLTTALILTA at the N-terminus. However, amino acid position number 1 in any fHbp is still defined herein as the position that corresponds to the cysteine at amino acid position 1 shown above for fHbp ID 1 in an alignment, which amino acid is the first residue after the leader sequence, if present.

FIG. 4 shows an alignment of fHbp sequences of variant 1, 2, and 3 fHbps. Note that the amino acid position 230 in fHbp ID 28 (variant 3) or fHbp ID 79 (variant 3) corresponds to amino acid position 223 of fHbp ID 1. With reference to v. 2 fHbp (e.g., fHbp ID22), the amino acid position is 222. H223 is indicated with an arrow. The alignment was performed using ClustalW available at European Bioinformatic Institute website. Amino acid identity is represented by an asterisk; strong similarity is represented by a colon; weak similarity is represented by a period; no similarity is represented by a blank space.

The present disclosure provides non-naturally occurring fHbps derived from a naturally occurring variant 3 fHbp (v. 3 fHbp), compositions comprising same, and methods of use of the fHbps non-naturally occurring and compositions. In certain embodiments, the non-naturally occurring fHbp comprises a substitution of the histidine at position 223 of the naturally occurring variant 3 fHbp with an amino acid selected from the group consisting of arginine, lysine, phenylalanine, tyrosine, or tryptophan, wherein the numbering of position 223 is based on the numbering of the mature fHbp ID 1, wherein the non-naturally occurring fHbp has lower affinity for human factor H (fH) than the naturally occurring variant 3 fHbp.

With reference to the sequence of fHbp ID 79 or fHbp ID 28, the histidine that is substituted in the non-naturally occurring fHbps described herein, corresponds to position 230. Specifically, the histidine that is mutated is the H within the sequence TYHLA (SEQ ID NO: 35) of the amino acid sequence of v. 3 fHbp.

Human factor H ("human fH") as used herein, refers to a protein comprising an amino acid sequence as shown below (SEQ ID NO: 3), and naturally-occurring human allelic variants thereof.

Human Factor H (fH)

MRLLAKIICLMLWAICVAEDCNELPPRRNTEILTGSWSDQTYPEGTQAIY

KCRPGYRSLGNVIMVCRKGEWVALNPLRKCQKRPCGHPGDTPFGTFTLTG

GNVFEYGVKAVYTCNEGYQLLGEINYRECDTDGWTNDIPICEVVKCLPVT

APENGKIVSSAMEPDREYHFGQAVRFVCNSGYKIEGDEEMHCSDDGFWSK

EKPKCVEISCKSPDVINGSPISQKIIYKENERFQYKCNMGYEYSERGDAV

CTESGWRPLPSCEEKSCDNPYIPNGDYSPLRIKHRTGDEITYQCRNGFYP

ATRGNTAKCTSTGWIPAPRCTLKPCDYPDIKHGGLYHENMRRPYFPVAVG

KYYSYYCDEHFETPSGSYWDHIHCTQDGWSPAVPCLRKCYFPYLENGYNQ

NHGRKFVQGKSIDVACHPGYALPKAQTTVTCMENGWSPTPRCIRVKTCSK

SSIDIENGFISESQYTYALKEKAKYQCKLGYVTADGETSGSIRCGKDGWS

AQPTCIKSCDIPVFMNARTKNDFTWFKLNDTLDYECHDGYESNTGSTTGS

IVCGYNGWSDLPICYERECELPKIDVHLVPDRKKDQYKVGEVLKFSCKPG

FTIVGPNSVQCYHFGLSPDLPICKEQVQSCGPPPELLNGNVKEKTKEEYG

HSEVVEYYCNPRFLMKGPNKIQCVDGEWTTLPVCIVEESTCGDIPELEHG

WAQLSSPPYYYGDSVEFNCSESFTMIGHRSITCIHGVWTQLPQCVAIDKL

KKCKSSNLIILEEHLKNKKEFDHNSNIRYRCRGKEGWIHTVCINGRWDPE

VNCSMAQIQLCPPPPQIPNSHNMTTTLNYRDGEKVSVLCQENYLIQEGEE

ITCKDGRWQSIPLCVEKIPCSQPPQIEHGTINSSRSSQESYAHGTKLSYT

CEGGFRISEENETTCYMGKWSSPPQCEGLPCKSPPEISHGVVAHMSDSYQ

YGEEVTYKCFEGFGIDGPAIAKCLGEKWSHPPSCIKTDCLSLPSFENAIP

MGEKKDVYKAGEQVTYTCATYYKMDGASNVTCINSRWTGRPTCRDTSCVN

PPTVQNAYIVSRQMSKYPSGERVRYQCRSPYEMFGDEEVMCLNGNWTEPP

QCKDSTGKCGPPPPIDNGDITSFPLSVYAPASSVEYQCQNLYQLEGNKRI

TCRNGQWSEPPKCLHPCVISREIMENYNIALRWTAKQKLYSRTGESVEFV

CKRGYRLSSRSHTLRTTCWDGKLEYPTCAKR

Naturally occurring fHbp has a high probability to be complexed with fH, the bound fH can mask one or more epitopes on the fHbp from a host's immune system. Accordingly, fHbp that is complexed and/or bound with fH may not be as effective an immunogen as an fHbp that is not so complexed. Conversely, fHbps that have a relatively low affinity for fH, when administered as an immunogen (e.g., in a vaccine composition), can present epitopes to the immune system of an immunized host that an fHbp that has high affinity for fH does not. The non-naturally occurring fHbps disclosed herein have a low affinity for human fH and are useful in eliciting bactericidal antibodies and/or providing protective immunity against N. meningitidis. A non-naturally occurring fHbp is not found in nature and is made by a human and/or intentionally modified by a human. A non-naturally occurring subject fHbp can be made via chemical synthesis or recombinant methods. A non-naturally occurring fHbp includes a mutation relative to the naturally occurring fHbp from which it was derived. As such, comprises a non-naturally occurring fHbp of the present disclosure includes a non-naturally occurring fHbp amino acid sequence.

As used herein, "low affinity", "lower affinity", or "low fH binder" refers to fHbps that have a binding affinity for a human fH that is lower than that of a v. 3 fHbp (e.g., fHbp ID79).

The binding affinity of the non-naturally occurring fHbps disclosed herein and human fH is 85% or less of the binding affinity of a wildtype v. 3 fHbp for human fH. For example, in some embodiments, the binding affinity of a subject non-naturally occurring fHbp for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of a wildtype fHbp for human fH. As an example, in some embodiments, the binding affinity of a subject non-naturally occurring fHbp for human fH is from about 85% to about 75%, from about 75% to about 65%, from about 65% to about 55%, from about 55% to about 45%, from about 45% to about 35%, from about 35% to about 25%, from about 25% to about 15%, from about 15% to about 10%, from about 10% to about 5%, from about 5% to about 2%, from about 2% to about 1%, or from about 1% to about 0.1%, or less than 0.1%, of the binding affinity of v. 3 fHbp for human fH.

Binding affinity can be described in terms of the dissociation constant ($K_D$). The subject non-naturally occurring fHbps and human fH can have a dissociation constant ($K_D$; M) that is at least more than about 80%, at least more than about 100%, at least more than about 120%, at least more than about 140%, at least more than about 160%, at least more than about 200%, or more than $K_D$ of wild type fHbp (such as, v. 3 fHbps, e.g., fHbp ID 79 or fHbp ID 28) and human fH. The $K_D$ of a subject non-naturally occurring fHbp can also be described as about 2× (2 times), about 3×, about 5×, about 10×, about 15×, about 20×, up to about 50 or more times the $K_D$ of fHbp ID 79. For example, a subject non-naturally occurring fHbp and human fH can have a $K_D$ that is 110% of or about 15× that of fHbp ID 79 and human fH.

As stated above, the subject non-naturally occurring fHbps are derived from a v. 3 fHbp. fHbp classified as variant group 3 (v. 3) are described in Masignani et al (2003) J Exp Med 197:789-99 and Pajon R et al (2010) Vaccine 28:2122-9. A list of known v. 3 fHbps and GenBank Accession numbers are provided in Beernink P T and Granoff D. M. (2009) Microbiology. 2009 September; 155 (Pt 9):2873-83. Table 1 shows a list of exemplary v. 3 fHbp including the source N. meningitidis strain, the capsular group, and corresponding modular group, peptide ID, GenBank Accession Number.

TABLE 1

| Source Strain | Capsular Group | Variant Group‡ | fHbp SubFamily§ | fHbp Peptide ID\|\| | fHbp Modular Group* | GenBank Accession Number |
|---|---|---|---|---|---|---|
| CDC-1135 | Y | 3 | A | 46 | II | AAR84437 |
| M1239 | B | 3 | A | 28 | II | ABF82029 |
| 03S-0451 | B | 3 | A | 76 | II | ACJ04735 |
| 03S-0669 | B | 3 | A | 29 | II | GQ219776 |
| SK104 | B | 3 | A | 99 | II | GQ219769 |
| M01 240988 | B | 3 | A | 30 | II | ACA52541 |
| M06 240137 | B | 3 | A | 64 | II | ACB38148 |
| M98 250771 | B | 3 | A | 45 | V | AAR84436 |
| M97 252153 | B | 3 | A | 47 | V | AAR84438 |
| S3032 | B | 3 | A | 79 | V | ACH48234 |
| M08 240023 | B | 3 | A | 84 | V | ACM44943 |
| C2120 | C | 3 | A | 59 | V | ABC59061 |
| MD1475 | B | 3 | A | 82 | V | GQ219772 |
| M01 240355 | B | 3 | A | 31 | V | ACB38139 |
| M08 240109 | B | 3 | A | 85 | V | ACM44944 |
| M06 240138 | B | 3 | A | 70 | V | ACM44938 |
| M01 242162 | B | 3 | A | 72 | V | ACM44939 |
| MA-5756 | C | 3 | A | 67 | VIII | Not Available† |
| 19498 | B | 3 | A | 175 | IX | ACI46928 |

‡Variant group defined by Masignani et al (2003)
§Subfamily as defined by Fletcher et al (2004)
\|\|Peptide identification number in the fHbp peptide database at neisseria.org
*Modular group defined by different combinations of the five respective α and β segments. Group II is composed entirely of β tye segments, while group V is composed of natural chimera of α and β segments.
†Sequence of fHbp ID 67 is available at Public databases for molecular typing and microbial genome diversity (at pubmlst.org) and is also provided here (see SEQ ID NO: 21).

The amino acid sequences of some examples of naturally-occurring v. 3 fHbps are shown below. Although the v. 3 fHbps include a leader sequence, the sequences shown below do not include this leader sequence and instead start at a cysteine residue which corresponds to position 1 with reference to the fHbp ID1 sequence provided above.

FHbp ID 28

(SEQ ID NO: 4)
CSSGGGGSGGGGVAADIGTGLADALTAPLDHKDKGLKSLTLEDSIPQNGT

LTLSAQGAEKTFKAGDKDNSLNTGKLKNDKISRFDFVQKIEVDGQTITLA

SGEFQIYKQNHSAVVALQIEKINNPDKTDSLINQRSFLVSGLGGEHTAFN

QLPGGKAEYHGKAFSSDDPNGRLHYSIDFTKKQGYGRIEHLKTLEQNVEL

AAAELKADEKSHAVILGDTRYGSEEKGTYHLALFGDRAQEIAGSATVKIG

EKVHEIGIAGKQ fHbp ID 46

(SEQ ID NO: 5)
CSSGGGGSGGGGVAADIGTGLADALTAPLDHKDKGLKSLTLEDSIPQNGT

LTLSAQGAEKTFKAGDKDNSLNTGKLKNDKISRFDFVQKIEVDGQTITLA

SGEFQIYKQDHSAVVALQIEKINNPDKIDSLINQRSFLVSGLGGEHTAFN

QLPGGKAEYHGKAFSSDDPNGRLHYSIDFTKKQGYGGIEHLKTPEQNVEL

ASAELKADEKSHAVILGDTRYGSEEKGTYHLALFGDRAQEIAGSATVKIG

EKVHEIGIAGKQ fHbp ID 76

(SEQ ID NO: 6)
CSSGGGGSGGIAADIGTGLADALTAPLDHKDKGLKSLTLEDSIPQNGTLT

LSAQGAEKTFKAGDKDNSLNTGKLKNDKISRFDFVQKIEVDGQTITLASG

EFQIYKQDHSAVVALQIEKINNPDKIDSLINQRSFLVSGLGGEHTAFNQL

PGGKAEYHGKAFSSDDPNGRLHYSIDFTKKQGYGRIEHLKTPEQNVELAS

AELKADEKSHAVILGDTRYGSEEKGTYHLALFGDRAQEIAGSATVKIREK

VHEIGIAGKQ fHbp ID 29

(SEQ ID NO: 7)
CSSGGGGSGGGGVAADIGAGLADALTAPLDHKDKGLKSLTLEDSIPQNGT

LTLSAQGAEKTFKAGGKDNSLNTGKLKNDKISRFDFVQKIEVDGQTITLA

SGEFQIYKQDHSAVVALQIEKINNPDKTDSLINQRSFLVSGLGGEHTAFN

QLPGGKAEYHGKAFSSDDPNGRLHYTIDFTNKQGYGRIEHLKTPEQNVEL

ASAELKADEKSHAVILGDTRYGSEEKGTYHLALFGDRAQEIAGSATVKIG

EKVHEIGIAGKQ fHbp ID 99

(SEQ ID NO: 8)
CSSGGGGSGGGGVAADIGTGLADALTAPLDHKDKGLKSLTLEDSIPQNGT

LTLSAQGAEKTFKAGDKDNSLNTGKLKNDKISRFDFVQKIEVDGQTITLA

SGEFQIYKQDHSAVVALQIEKINNPDKIDSLINQRSFLVSGLGGEHTAFN

QLPGGKAEYHGKAFSSDDPNGRLHYSIDFTKKQGYGRIEHLKTPEQNVEL

ASAELKADEKSHAVILGDTRYGSEEKGTYHLALFGDRAQEIAGSATVKIG

EKVHEIGIAGKQ fHbp ID 30

(SEQ ID NO: 9)
CSSGGGGSGGGGVAADIGTGLADALTAPLDHKDKGLKSLTLEDSIPQNGT
LTLSAQGAEKTFKAGDKDNSLNTGKLKNDKISRFDFVQKIEVDGQTITLA
SGEFQIYKQNHSAVVALQIEKINNPDKIDSLINQRSFLVSGLGGEHTAFN
QLPGDKAEYHGKAFSSDDPNGRLHYTIDFTNKQGYGRIEHLKTPELNVDL
ASAELKADEKSHAVILGDTRYGSEEKGTYHLALFGDRAQEIAGSATVKIG
EKVHEIGIAGKQ fHbp ID 64

(SEQ ID NO: 10)
CSSGSGGGGVAADIGTGLADALTAPLDHKDKGLKSLTLEDSIPQNGTLTL
SAQGAEKTFKAGDKDNSLNTGKLKNDKISRFDFVQKIEVDGQTITLASGE
FQIYKQNHSAVVALQIEKINNPDKIDSLINQRSFLVSGLGGEHTAFNQLP
GGKAEYHGKAFSSDDPNGRLHYTIDFTNKQGYGRIEHLKTPELNVDLASA
ELKADEKSHAVILGDTRYGSEEKGTYHLALFGDRAQEIAGSATVKIGEKV
HEIGIAGKQ fHbp ID 45

(SEQ ID NO: 11)
CSSGSGSGGGGVAADIGTGLADALTAPLDHKDKGLKSLTLEDSISQNGTL
TLSAQGAEKTFKVGDKDNSLNTGKLKNDKISRFDFVQKIEVDGQTITLAS
GEFQIYKQDHSAVVALQIEKINNPDKIDSLINQRSFLVSGLGGEHTAFNQ
LPSGKAEYHGKAFSSDDAGGKLTYTIDFAAKQGHGKIEHLKTPEQNVELA
SAELKADEKSHAVILGDTRYGSEEKGTYHLALFGDRAQEIAGSATVKIRE
KVHEIGIAGKQ fHbp ID 47

(SEQ ID NO: 12)
CSSGGGGVAADIGAGLADALTAPLDHKDKGLKSLTLEDSISQNGTLTLSA
QGAEKTFKVGDKDNSLNTGKLKNDKISRFDFVQKIEVDGQTITLASGEFQ
IYKQNHSAVVALQIEKINNPDKIDSLINQRSFLVSGLGGEHTAFNQLPGG
KAEYHGKAFSSDDAGGKLTYTIDFAAKQGHGKIEHLKTPEQNVELAAAEL
KADEKSHAVILGDTRYGSEEKGTYHLALFGDRAQEIAGSATVKIGEKVHE
ISIAGKQ fHbp ID 79

(SEQ ID NO: 13)
CSSGGGGSGSGGVAADIGTGLADALTTPLDHKDKGLKSLTLEDSIPQNGT
LTLSAQGAEKTFKAGDKDNSLNTGKLKNDKISRFDFVQKIEVDGQTITLA
SGEFQIYKQDHSAVVALQIEKINNPDKIDSLINQRSFLVSGLGGEHTAFN
QLPGGKAEYHGKAFSSDDAGGKLTYTIDFAAKQGHGKIEHLKTPEQNVEL
ASAELKADEKSHAVILGDTRYGSEEKGTYHLALFGDRAQEIAGSATVKIG
EKVHEIGIAGKQ fHbp ID 84

(SEQ ID NO: 14)
CSSGGGGSGGGGVAADIGTGLADALTAPLDHKDKGLKSLTLEDSIPQNGT
LTLSAQGAEKTFKAGDKDNSLNTGKLKNDKISRFDFVQKIEVDGQTITLA
SGEFQIYKQDHSAVVALQIEKINNPDKIDSLINQRSFLVSGLGGEHTAFN
QLPGGKAEYHGKAFSSDDAGGKLTYTIDFAAKQGHGKIEHLKTPEQNVEL
AAAELKADEKSHAVILGDTRYDSEEKGTYHLALFGDRAQEIAGSATVKIG
EKVHEISIAGKQ fHbp ID 59

(SEQ ID NO: 15)
CSSGGGGSGSGGVAADIGTGLADALTTPLDHKDKGLKSLTLEDSIPQNGT
LTLSAQGAEKTFKAGDKDNSLNTGKLKNDKISRFDFVQKIEVDGQTITLA
SGEFQIYKQDHSAVVALQIEKINNPDKIDSLINQRSFLVSGLGGEHTAFN
QLPGGKAEYHGKAFSSDDAGGKLTYTIDFASKQGHGKIEHLKTPEQNVEL
AAAELKADEKSHAVILGDTRYGSEEKGTYHLALFGDRAQEIAGSATVKIG
EKVHEIGIAGKQ fHbp ID 82

(SEQ ID NO: 16)
CSSGGGGVAADIGTGLADALTAPLDHKDKGLKSLTLEDSIPQNGTLTLSA
QGAEKTFKAGDKDNSLNTGKLKNDKISRFDFVQKIEVDGQTITLASGEFQ
IYKQNHSAVVALQIEKINNPDKIDSLINQRSFLVSGLGGEHTAFNQLPVG
KAEYHGKAFSSDDAGGKLTYTIDFAAKQGHGKIEHLKSPELNVELATAEL
KADEKSHAVILGDTRYGSEEKGTYHLALFGDRAQEIAGSATVKIREKVHE
IGIAGKQ fHbp ID 31

(SEQ ID NO: 17)
CSSGGGGSGSGGVAADIGTGLADALTTPLDHKDKGLKSLTLEDSIPQNGT
LTLSAQGAEKTFKAGDKDNSLNTGKLKNDKISRFDFVQKIEVDGQTITLA
SGEFQIYKQDHSAVVALQIEKINNPDKIDSLINQRSFLVSGLGGEHTAFN
QLPGGKAEYHGKAFSSDDAGGKLTYTIDFAAKQGHGKIEHLKTPEQNVEL
AAAELKADEKSHAVILGDTRYGSEEKGTYHLALFGDRAQEIAGSATVKIG
EKVHEIGIAGKQ fHbp ID 85

(SEQ ID NO: 18)
CSSGGGGSGSGGVAADIGTGLADALTTPLDHKDKGLKSLTLEDSIPQNGT
LTLSAQGAEKTFKAGDKDNSLNTGKLKNDKISRFDFVQKIEVDGQTITLA
SGEFQIYKQDHSAVVALQIEKINNPDKIDSLINQRSFLVSGLGGEHTAFN
QLPSGKAEYHGKAFSSDDAGGKLTYTIDFAAKQGHGKIEHLKTPEQNVEL
ASAELKADEKSHAVILGDTRYGSEEKGTYHLALFGDRAQEIAGSATVKIR
EKVHEIGIAGKQ fHbp ID 70

(SEQ ID NO: 19)
CSSGGGGSGGGGVAADIGAGLADALTAPLDHKDKGLKSLTLEDSIPQNGT

LTLSAQGAEKTFKAGDKDNSLNTGKLKNDKISRFDFVQKIEVDGQTITLA

SGEFQIYKQDHSAVVALQIEKINNPDKIDSLINQRSFLVSGLGGEHTAFN

QLPGGKAEYHGKAFSSDDAGGKLTYTIDFAAKQGHGKIEHLKTPEQNVEL

AAAELKADEKSHAVILGDTRYGSEEKGTYHLALFGDRAQEIAGSATVKIG

EKVHEIGIAGKQ fHbp ID 72

(SEQ ID NO: 20)
CSSGGGGSGGVAADIGTGLADALTTPLDHKDKGLKSLTLEDSIPQNGTLT

LSAQGAEKTFKAGDKDNSLNTGKLKNDKISRFDFVQKIEVDGQTITLASG

EFQIYKQDHSAVVALQIEKINNPDKIDSLINQRSFLVSGLGGEHTAFNQL

PGGKAEYHGKAFSSDDAGGKLTYTIDFAAKQGHGKIEHLKTPEQNVELAA

AELKADEKSHAVILGDTRYGSEEKGTYHLALFGDRAQEIAGSATVKIGEK

VHEIGIAGKQ fHbp ID 67

(SEQ ID NO: 21)
CSSGGGGSGGGGVAADIGAGLADALTAPLDHKDKGLKSLTLEDSISQNGT

LTLSAQGAERTFKAGDKDNSLNTGKLKNDKISRFDFIRQIEVDGQLITLE

SGEFQIYKQDHSAVVALQIEKINNPDKIDSLINQRSFLVSGLGGEHTAFN

QLPSGKAEYHGKAFSSDDPNGRLHYSIDFTKKQGYGRIEHLKTPEQNVEL

ASAELKADEKSHAVILGDTRYGGEEKGTYHLALFGDRAQEIAGSATVKIR

EKVHEIGIAGKQ fHbp ID 175

(SEQ ID NO: 22)
CSSGGGGSGGGGVAADIGAGLADALTAPLDHKDKGLKSLTLEDSISQNGT

LTLSAQGAERTFKAGDKDNSLNTGKLKNDKISRFDFIRQIEVDGQLITLE

SGEFQIYKQDHSAVVALQIEKINNPDKIDSLINQRSFLVSGLGGEHTAFN

QLPDGKAEYHGKAFSSDDAGGKLTYTIDFAAKQGHGKIEHLKTPEQNVEL

AAAELKADEKSHAVILGDTRYGSEEKGTYHLALFGDRAQEIAGSATVKIG

EKVHEIGIAGKQ

As noted above, the non-naturally occurring fHbps disclosed herein may be derived from a naturally occurring v. 3 fHbp. Exemplary v. 3 fHbp are listed above. Naturally-occurring fHbps have variable segments derived from different progenitors (α and/or β). Due to the variable segments, the molecular architecture has been shown to be modular and fHbp variants can be subclassified in modular groups according to different combinations of five variable segments (A, B, C, D, and E), each derived from one of two genetic lineages, designated α- or β-types (Pajon R et al. (2010) *Vaccine* 28:2122-9; Beernink P T, Granoff D M (2009) *Microbiology* 155:2873-83). Six modular groups, designated I to VI account for >95% of all known fHbp variants (Pajon R et al. (2010) *Vaccine* 28:2122-9).

Figure 6:
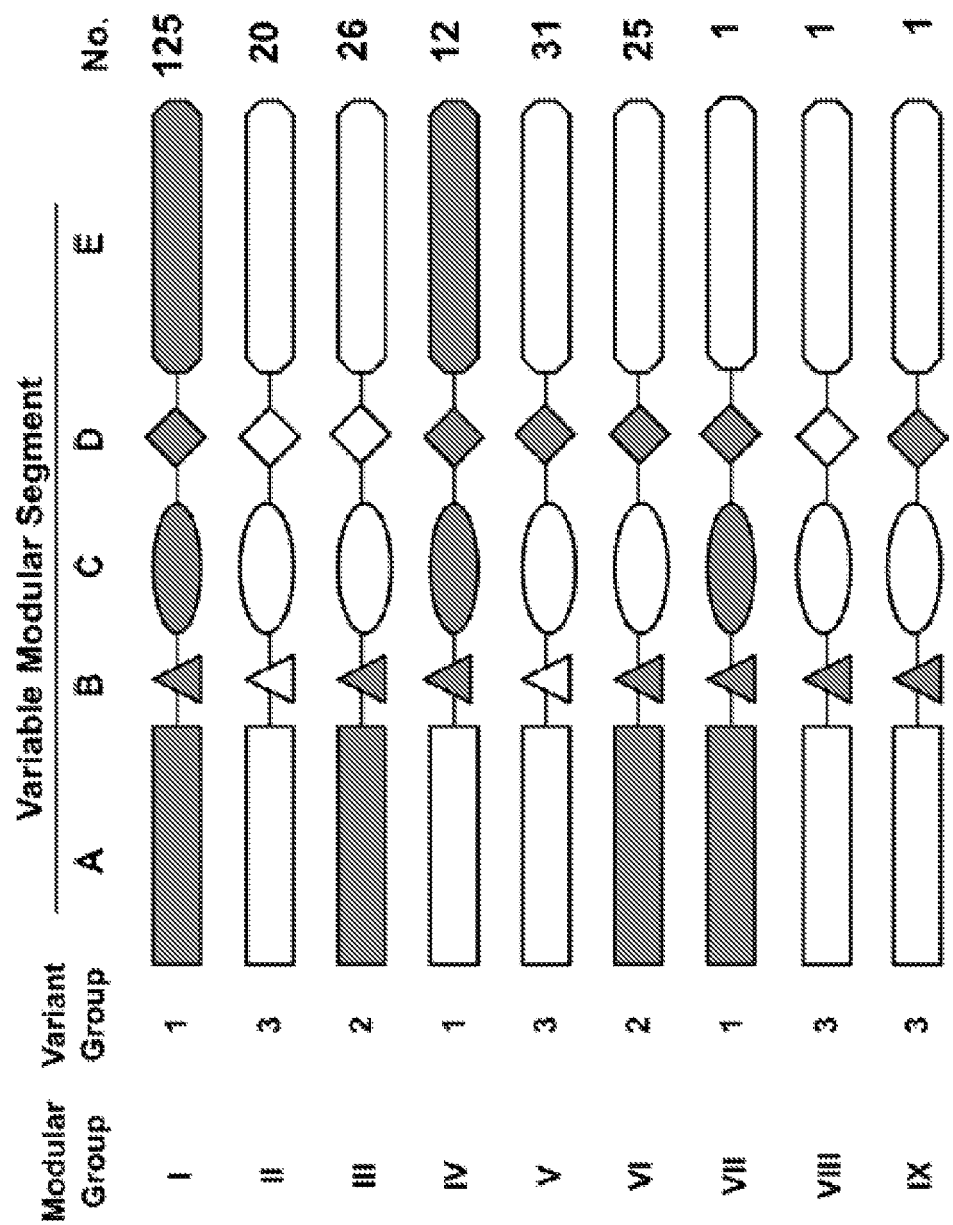
FIG. 6. A schematic representation of fHbp modular groups I-IX.
Figure 7:
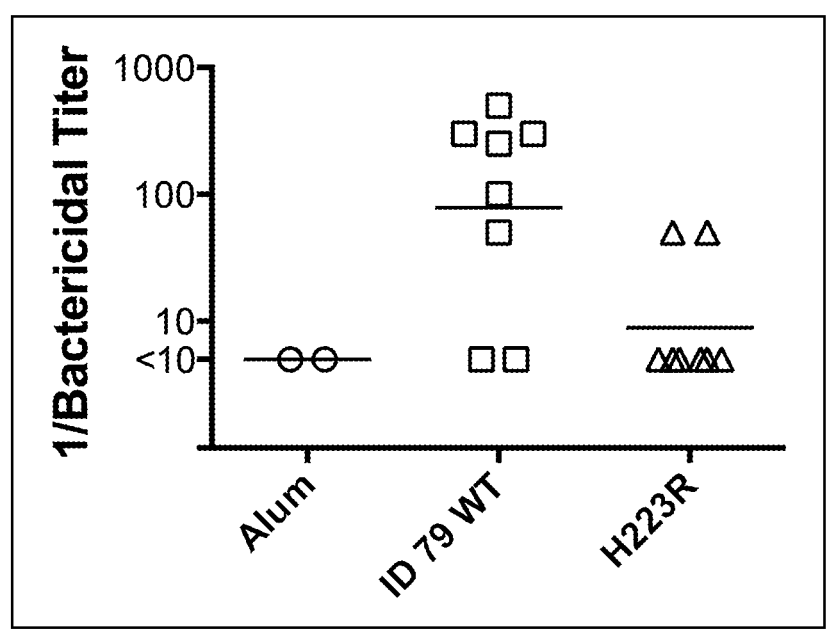
FIG. 7. A graph showing bactericidal responses of mice to fHbp ID 79 vaccines. fHbp ID 79 wild-type (WT) and fHbp ID 79 H223R mutant were tested. For the fHbp vaccines, each symbol represents the titer of an individual serum sample; for the aluminum (Alum) control group, each symbol represents the titer of a pool of three serum samples. The horizontal lines represent the geometric mean titer for each group.

A schematic representation of fHbp modular structure is provided in FIG. 6. Schematic of nine fHbp modular groups deduced from phylogenic analysis of 242 unique amino acid variants are shown. The respective Masignani variant group designations, and the number of unique sequences observed within each fHbp modular group, are shown. Variable segments derived from α lineage are depicted in grey and those derived from β lineage are depicted in white.

In certain embodiments, the v. 3 fHbp may be a modular group II fHbp. Group II fHbps are composed entirely of β type segments (fHbp variable segments: $A_\beta$, $B_\beta$, $C_\beta$, $D_\beta$, and $E_\beta$). Exemplary modular group II fHbp are provided in Table 1.

In certain embodiments, the v. 3 fHbp may be a modular group V fHbp. Modular group V fHbps are composed of natural chimera of α and β segments and have the following fHbp variable segments from the designated progenitors: $A_\beta$, $B_\beta$, $C_\beta$, $D_\beta$, and $E_\beta$. Exemplary modular group V fHbp are provided in Table 1.

In certain embodiments, the v. 3 fHbp may be a modular group VIII fHbp. Modular group VIII fHbps are composed of α and β segments and have the following fHbp variable segments from the designated progenitors: $A_\beta$, $B_\beta$, $C_\beta$, $D_\beta$, and $E_\beta$. Exemplary modular group VIII fHbp are provided in Table 1.

In certain embodiments, the v. 3 fHbp may be a modular group IX fHbp. Modular group IX fHbps are composed of α and β segments and have the following fHbp variable segments from the designated progenitors: $A_\beta$, $B_\beta$, $C_\beta$, $D_\beta$, and $E_\beta$. Exemplary modular group IX fHbp are provided in Table 1.

In certain embodiments, the non-naturally occurring fHbp comprising a substitution of the histidine at position 223 of a naturally occurring variant 3 fHbp with an amino acid selected from the group consisting of arginine, lysine, phenylalanine, tyrosine, or tryptophan, may have an amino acid sequence that is at least 90% identical to the amino acid sequences of the naturally occurring variant 3 fHbp. In certain cases, the identity may be within a segment (e.g., variable segment as defined in a modular architecture), in two or more variable segments, or in the full-length mature protein.

The subject non-naturally occurring fHbp can comprise an amino acid sequence having at least 90%, at least 95%, at least 98%, at least 99%, amino acid sequence identity with a variant 3 fHbp (for example, fHbp 79). In certain cases, the subject non-naturally occurring fHbp may differ from the amino acid sequence of the v. 3 fHbp by from 1 amino acid (aa) to 25 amino acids, e.g., differs from the amino acid sequence of the v. 3 fHbp by 1 aa, 2 aa, 3 aa, 4 aa, 5 aa, 6 aa, 7 aa, 8 aa, 9 aa, 10 aa, 13 aa, 15 aa, 18 aa, 20 aa, 22 aa, 24 aa, or 25 aa. Thus, e.g., a subject non-naturally occurring fHbp can have at most one, at most two, at most three, at most four, at most six, at most eight, at most ten, at most twelve, at most fourteen, at most sixteen, at most eighteen, up to at most 25 or more modifications (e.g. substitutions, deletions, or insertions) relative to a v. 3 fHbp from which the subject fHbp is derived. The one or more amino acid alterations can decrease the affinity of the fHbp for human fH relative to a fHbp that is not altered.

In some embodiments, a subject non-naturally occurring fHbp comprises a substitution of the histidine at position 223 of a naturally occurring variant 3 fHbp with arginine. As noted above, the v. 3 fHbp may be fHbp ID 46, fHbp ID 28, fHbp ID 76, fHbp ID 29, fHbp ID 99, fHbp ID 30, fHbp ID 64, fHbp ID 45, fHbp ID 47, fHbp ID 79, fHbp ID 84, fHbp ID 59, fHbp ID 82, fHbp ID 31, fHbp ID 85, fHbp ID 70, fHbp ID 72, fHbp ID 67, or fHbp ID 175.

An alignment of exemplary v. 3 fHbps is provided in FIGS. 5A-5E. The position of H223 is also indicated. The reference sequence, fHbp ID 1, is also included in the alignment. Notably, fHbp ID 1 does not have a histidine at position 223. The alignment was performed using ClustalW available at European Bioinformatic Institute website. Amino acid identity is represented by an asterisk; strong similarity is represented by a colon; weak similarity is represented by a period; no similarity is represented by a blank space.

As shown herein, a fHbp derived from v. 3 fHbp and that contains H223R substitution has decreased binding to human fH relative to the naturally-occurring v. 3 fHbp. Thus, non-naturally fHbp containing the amino acid substitution that is conservative relative to the arginine substitution are also expected to have decreased binding to human fH compared to the naturally-occurring v. 3 fHbp. As such, the present disclosure contemplates conservative amino acid substitutions relative to arginine (R), such as the amino acid substitutions H223K is also contemplated. Additionally, an amino acid substitution that provides steric hinderance to the binding of fH to fHbp are also contemplated-exemplary amino acid substitutions include substitution with an amino acid having a bulky hydrophobic side chain, such as phenylalanine, tyrosine, and trypstophan. As such, the amino acid substitutions H223F, H223Y, and H223W are also contemplated.

In general, the subject non-naturally occurring fHbp does not include a substitution of the histidine at position 223 with alanine.

One feature of a subject non-naturally occurring fHbp is that when administered to a host (e.g., mammals such as mice or human), the subject fHbp can elicit a bactericidal response at a level comparable or higher than the bactericidal response elicited by the v. 3 fHbp from which it was derived (e.g. fHbp ID 79, 46, 28, 67, 175, or 59). Methods for determining levels of bactericidal response are known in the art. In certain cases, the geometric mean bactericidal titers of mice immunized with the subject fHbp is at least about 70%, at least about 80%, at least about 85%, at least about 90%, at least about 95%, at least about 100%, at least about 110%, at least about 120%, at least about 150%, at least about 175%, at least about 200%, or more than 200%, of the geometric mean bactericidal titers of mice immunized with a variant 3 fHbp (e.g., fHbp ID 79). In some instances, the geometric mean bactericidal titer of a mouse immunized with a subject fHbp is at least 2-fold, at least 2.5-fold, at least 5-fold, at least 10-fold, or more than 10-fold, higher than the geometric mean bactericidal titer of a control mouse immunized with a variant 3 fHbp (e.g., fHbp ID 79). The subject fHbps can exclude those that elicit a bactericidal response significantly lower than that elicited by a variant 3 fHbp (e.g., fHbp ID 79).

In many cases, a subject non-naturally occurring fHbp maintains and presents a conformational epitope bound by antibodies that have bactericidal activity toward one or more *Neisseria meningitidis* strains. Thus, such fHbp mutants may maintain an epitope found in a naturally-occurring v. 3 fHbp, while exhibiting reduced binding to fH compared to the binding affinity for fH of the naturally-occurring v. 3 fHbp. Mutants that have minimal or no effect on the conformation of fHbp such that the mutant fHbp elicits bactericidal antibodies are considered good vaccine candidates. Whether a mutant has an effect on the conformation of fHbp can be determined in various ways, including binding of JAR 31, JAR 33, or JAR 11 antibodies. Accordingly, a non-naturally occurring fHbp disclosed herein may bind to JAR 31, JAR 33, or JAR 11 antibodies.

The fHbps of the present disclosure may have additional features, described in more detail below.

Chimeric fHbps

A non-naturally occurring fHbp of the present disclosure may be a chimeric fHbp. A chimeric fHbp of the present disclosure may be described as having N-terminal domain (fHbpN) of fHbp from a variant group 1 or 2 (v. 1 or v. 2 fHbp) while the C-terminal domain (fHbpC) may be derived from a v. 3 fHbp (e.g. fHbp ID 79), the non-naturally occurring fHbp comprising a substitution of the histidine at position 223 of the naturally occurring variant 3 fHbp with an amino acid selected from the group consisting of arginine, lysine, phenylalanine, tyrosine, or tryptophan.

In certain embodiments, the chimeric non-naturally occurring fHbp of the present disclosure may have a fHbpN domain of fHbp from a variant group 1 (e.g., fHbp ID 1) and fHbpC domain derived from a v. 3 fHbp (e.g. fHbp ID 28), the chimeric non-naturally occurring fHbp comprising a substitution of the histidine at position 223 of the naturally occurring variant 3 fHbp with an amino acid selected from the group consisting of arginine, lysine, phenylalanine, tyrosine, or tryptophan.

In certain embodiments, the chimeric non-naturally occurring fHbp of the present disclosure may have a fHbpN domain derived from a variant group 1 fHbp (e.g., fHbp ID 1) and fHbpC domain derived from a v. 3 fHbp (e.g. fHbp ID 79), the non-naturally occurring fHbp comprising a substitution of the histidine at position 223 of the naturally occurring variant 3 fHbp with an amino acid selected from the group consisting of arginine, lysine, phenylalanine, tyrosine, or tryptophan. In certain cases, the fHbpN domain may have a substitution of the arginine at position 41 of a naturally occurring v. 1 fHbp. In certain cases, the substitution may be R41S.

"fHbpN" refers to a contiguous amino acid sequence that starts at about residue position 8 and ends at about residue position 136. "fHbpC" refers to a contiguous amino acid sequence that starts at about residue position 141 and ends at about residue position 255. Intervening sequence between fHbpN and fHbpC is a linker between the two domains.

Exemplary chimeric fHbp that may be modified to include the H223R, H223W, H223F, H223Y, or H223K substitution may be any known man-made chimera, such as those described in Beernink et al. (2008) *Infec. Immun.* 76:2568-2575 and WO 2009/114485, disclosure of which is incorporated herein by reference. The chimera containing the substitution may have a decreased affinity for human fH relative to the corresponding chimeric fHbp, while still maintaining epitopes important for eliciting bactericidal response, such as those found in the corresponding chimeric fHbp. fHbp epitopes that may be maintained in the modified chimeric includes those that are found in the corresponding chimeric fHbp such as those described in WO 2009/114485, disclosure of which is incorporated herein by reference. For example, a modified chimeric fHbp can contain epitopes important for eliciting bactericidal antibody response against strains containing variant 1 fHbp (e.g. epitopes in the N-terminal domain such as those defined by mAb JAR 4 and/or JAR 5) and/or against strains containing variant 2 and/or 3 fHbp (e.g. epitopes defined by mAb JAR 10, JAR 11, JAR 13, and/or JAR 36).

Exemplary Chimera are shown below:
Chimera 1/79

(SEQ ID NO: 23)
cssgggggvaadigagladaltapldhkdkglqsltldqsvrkneklklaa qgaektygngdslntgklkndkvsrfdfirqievdgqlitlesgefqvyk qshsaltafqteqiqdsehsgkmvakrqfrigdiaGEHTAFNQLPGGKAE

YHGKAFSSDDAGGKLTYTIDFAAKQGHGKIEHLKTPEQNVELASAELKAD

EKSHAVILGDTRYGSEEKGTY<u>H</u>LALFGDRAQEIAGSATVKIGEKVHEIGI

AGKQ.

The lower case letters correspond to the amino acid sequence that is derived from fHbp ID 1 while the upper case letters correspond to the amino acid that is derived from fHbp ID 79. Position corresponding to H223 in fHbp ID 79 is the bolded and underlined. Accordingly, the chimeric non-naturally occurring fHbp of the present disclosure may include the sequence of Chimera 1/79 with a substitution of H223 into H223R, H223W, H223F, H223Y, or H223K.

Chimera 1(R41S)/79

(SEQ ID NO: 24)
cssgggggvaadigagladaltapldhkdkglqsltldqsvskneklklaa qgaektygngdslntgklkndkvsrfdfirqievdgqlitlesgefqvyk qshsaltafqteqiqdsehsgkmvakrqfrigdiaGEHTAFNQLPGGKAE

YHGKAFSSDDAGGKLTYTIDFAAKQGHGKIEHLKTPEQNVELASAELKAD

EKSHAVILGDTRYGSEEKGTY<u>H</u>LALFGDRAQEIAGSATVKIGEKVHEIGI

AGKQ.

The lower case letters correspond to the amino acid sequence that is derived from fHbp ID 1 while the upper case letters correspond to the amino acid that is derived from fHbp ID 79. Position 41 includes a substitution of the R with a serine. Position corresponding to H223 in fHbp ID 79 is the bolded and underlined. Accordingly, the chimeric non-naturally occurring fHbp of the present disclosure may include the sequence of Chimera 1(R41S)/79 with a substitution of H223 into H223R, H223W, H223F, H223Y, or H223K.

In general, the subject non-naturally occurring fHbp does not include a substitution of the histidine at position 223 with alanine.

The subject non-naturally occurring chimeric fHbp can comprise an amino acid sequence having at least 90%, at least 95%, at least 98%, at least 99%, amino acid sequence identity with a variant 3 fHbp (for example, fHbp 79). The identity may be within the region of the subject chimeric fHbp derived from v. 3 fHbp and the corresponding region of the v. 3 fHbp. For example, in a chimeric protein where the fHbpC domain is derived from a v. 3 fHbp, the identity may be in the fHbp C domains.

One feature of a subject chimeric non-naturally occurring fHbp is that when administered to a host (e.g. mammals such as mice or human), the subject fHbp can elicit a bactericidal response at a level comparable or higher than the bactericidal response elicited by the variant group fHbps from which the chimera is derived (e.g. fHbp ID 1 and fHbp ID 79).

Methods for determining levels of bactericidal response are known in the art. In certain cases, the geometric mean bactericidal titers of mice immunized with the subject chimeric fHbp is at least about 70%, at least about 80%, at least about 85%, at least about 90%, at least about 95%, at least about 100%, at least about 110%, at least about 120%, at least about 150%, at least about 175%, at least about 200%, or more than 200%, of the geometric mean bactericidal titers of mice immunized with fHbp ID 1 or fHbp ID 79. In some instances, the geometric mean bactericidal titer of a mouse immunized with a subject fHbp is at least 2-fold, at least 2.5-fold, at least 5-fold, at least 10-fold, or more than 10-fold, higher than the geometric mean bactericidal titer of a control mouse immunized with fHbp ID 1 or fHbp ID 79.

The subject fHbps can exclude those that elicit a bactericidal response significantly lower than that elicited by fHbp ID 1 or fHbp ID 79.

In many cases, a subject non-naturally occurring chimeric fHbp maintains and presents a conformational epitope bound by bacterial antibodies that have bactericidal activity toward one or more *Neisseria meningitidis* strains. Thus, such fHbp mutants may maintain an epitope found in a naturally-occurring fHbp, while exhibiting reduced binding to fH compared to the binding affinity for fH of a naturally-occurring fHbp. Non-naturally occurring chimeric fHbp of the present disclosure that have minimal or no effect on the conformation of fHbp such that the chimeric fHbp elicits bactericidal antibodies are considered good vaccine candidates. Whether a variant has an effect on the conformation of fHbp can be determined in various ways, including binding of antibodies, such as, JAR 4, JAR 5, JAR 31, JAR 33, or JAR 11.

The fHbps of the present disclosure may have additional features, described in more detail below.

Conjugates

The subject fHbps of the present disclosure may contain one or more additional elements at the N- and/or C-terminus of the polypeptide, such as a polypeptide (e.g. having an amino acid sequence heterologous to the subject fHbp) and/or a carrier molecule. The additional heterologous amino acid sequences may be fused, e.g., to provide an N-terminal methionine or derivative thereof (e.g., pyroglutamate) as a result of expression in a bacterial host cell (e.g., *E. coli*) and/or to provide a chimeric polypeptide having a fusion partner at its N-terminus or C-terminus. Fusion partners of interest include, for example, glutathione-S-transferase (GST), maltose binding protein (MBP), His$_6$-tag, and the like, as well as leader peptides from other proteins, particularly lipoproteins. Fusion partners can provide for additional features, such as in facilitating isolation, purification, detection, immunogenicity of the subject fHbp.

Other elements that may be linked to the subject fHbp include a carrier molecule (e.g., a carrier protein, e.g. keyhole limpet hemocyanin (KLH)). Additional elements may be linked to the peptide via a linker, e.g. a flexible linker. Carriers encompass immunomodulators, a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid. Other carrier molecules that facilitate administration and/or to increase the immunogenicity in a subject to be vaccinated or treated against *N. meningitidis* are also contemplated. Carrier molecules can also facilitate delivery to a cell or tissue of interest. The additional moiety may also aid in immunogenicity or forming a complex with a component in a vaccine. The carrier molecules may act as a scaffold protein to facilitate display of the epitopes on a membrane surface (e.g. a vesicle vaccine).

In one example, the subject fHbps are modified at the N- and/or C-terminus to include a fatty acid (e.g. aliphatic carboxylic acid group). The fatty acid may be covalently linked to the fHbp via a flexible linker. An example of a fatty acid that may be used to modify an end (e.g. N-terminal end, e.g., at the N-terminus) of the subject fHbp is lauric acid. Lauric acid when covalently attached to another molecule is referred to as a lauroyl group (e.g. lauroyl sulfate). Lauric acid contains twelve carbon atoms with ten methylene groups and the formula $CH_3—(CH_2)_{10}—COOH$. Other fatty acids that may be linked to the subject peptides include caprylic acid (10 C), myristic acid (14 C), and palmitic acid (16 C). For details, see Westerink M A et al. (1995) *Proc. Natl. Acad. Sci. USA* 92:4021-4025. It is also contemplated that any hydrophobic moiety that can serve to anchor the subject fHbp into the bacterial outer membrane is contemplated herein for conjugation to a N- and/or C-terminal end (e.g., at the N-terminus) of the fHbps of the present disclosure, where the hydrophobic moiety can be optionally conjugated to the peptide through a linker, e.g., a flexible linker, as described herein. For example, a hydrophobic pentapeptide

FLLAV, (SEQ ID NO: 25)

as described in Lowell G H et al. (1988) *J. Exp. Med.* 167:658-63.

As noted above, one way in which the fatty acid, as well as other additional elements described above, is connected to the fHbp is via a linker (e.g. lauroyl-Gly-Gly). Linkers suitable for use in modifying the fHbp of the present disclosure include "flexible linkers". Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Examples of flexible linkers include glycine polymers $(G)_n$, glycine-serine polymers (including, for example, $(GS)_n$, $GSGGS_n$ (SEQ ID NO: 33) and $GGGS_n$ (SEQ ID NO: 34), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more Ramachandran (or phi-psi) space than even alanine, and are much less restricted than residues with longer side chains (see Scheraga, Rev. Computational Chem. 11173-142 (1992)). Exemplary flexible linkers include, but are not limited GGSG, (SEQ ID NO: 26)
GGSGG, (SEQ ID NO: 27)
GSGSG, (SEQ ID NO: 28)
GSGGG, (SEQ ID NO: 29)
GGGSG, (SEQ ID NO: 30)
GSSSG, (SEQ ID NO: 31)

and the like. The ordinarily skilled artisan will recognize that design of a fHbp conjugated to any elements described above can include linkers that are all or partially flexible, such that the linker can include a flexible linker as well as one or more portions that confer less flexible structure.

Native fHbp usually contains an N-terminal cysteine to which a lipid moiety can be covalently attached. This cysteine residue is usually lipidated in the naturally-occurring protein, and can be lipidated in the subject fHbps disclosed herein. Thus, in the amino acid sequences described herein, reference to "cysteine" or "C" at this position specifically includes reference to both an unmodified cysteine as well as to a cysteine that is lipidated (e.g., due to post-translational modification). Thus, the subject fHbp can be lipidated or non-lipidated. Methods for production of lipidated proteins in vitro, (see, e.g., Andersson et al. (2001) *J. Immunological Methods* 255:135-48) or in vivo are known in the art. For example, lipidated fHbp previously has been purified from the membrane fraction of *E. coli* protein by detergent extraction (Fletcher et al. (2004) *Infection and Immunity* 72:2088-100), which method may be adapted for the production of lipidated fHbp. Lipidated proteins may be of interest as such can be more immunogenic than soluble protein (see, e.g., Fletcher et al. (2004) Infection and Immunity 72:2088-100).

It will be appreciated that the nucleotide sequences encoding heterologous fHbps can be modified so as to optimize the codon usage to facilitate expression in a host cell of interest (e.g., *E. coli*, *N. meningitidis*, human (as in the case of a DNA-based vaccine), and the like). Methods for production of codon optimized sequences are known in the art.

Nucleic Acids Encoding fHbp

The present disclosure provides a nucleic acid encoding a subject fHbp. A subject nucleic acid will in some embodiments be present in a recombinant expression construct. Also provided are genetically modified host cells comprising a subject nucleic acid.

fHbp polypeptides, and encoding nucleic acids of the present disclosure can be derived from any suitable *N. meningitidis* strain. As is known in the art, *N. meningitidis* strains are divided into serologic groups (capsular groups), serotypes (PorB phenotypes) and subtypes (PorA phenotypes) on the basis of reactions with polyclonal (Frasch, C. E. and Chapman, 1973, *J. Infect. Dis.* 127: 149-154) or monoclonal antibodies that interact with different surface antigens. Capsular grouping traditionally has been based on immunologically detectable variations in the capsular polysaccharide but is being replaced by PCR of genes encoding specific enzymes responsible for the biosynthesis of the structurally different capsular polysaccharides. About 12 capsular groups (including A, B, C, X, Y, Z, 29-E, and W-135) are known. Strains of the capsular groups A, B, C, Y and W-135 account for nearly all meningococcal disease. Serotyping traditionally has been based on monoclonal antibody defined antigenic differences in an outer membrane protein called Porin B (PorB). Antibodies defining about 21 serotypes are currently known (Sacchi et al., 1998, *Clin. Diag. Lab. Immunol.* 5:348). Serosubtyping has been based on antibody defined antigenic variations on an outer membrane protein called Porin A (PorA). Both serotyping and serosubtyping are being replaced by PCR and/or DNA sequencing for identification of genes encoding the variable regions of PorB and PorA, respectively that are associated with mAb reactivity (e.g. Sacchi, Lemos et al., supra; Urwin et al., 1998, *Epidem. and Infect.* 120:257).

While *N. meningitidis* strains of any capsular group may be used, *N. meningitidis* strains of capsular group B can be sources from which nucleic acid encoding fHbp and domains thereof are derived.

Nucleic acids encoding fHbp polypeptides for use in construction of the subject fHbps contemplated herein are known in the art. Various fHbp and their sequences are available at neisseria.org and pubmlst.org/neisseria/fHbp websites. Examples of fHbp polypeptides are also described in, for example, U.S. patent application No. 61/174,424, PCT application number PCT/US09/36577, WO 2004/048404; Masignani et al. (2003) *J Exp Med* 197:789-799; Fletcher et al. (2004) *Infect Immun* 72:2088-2100; Welsch et al. J Immunol 2004 172:5606-5615; and WO 99/57280. Nucleic acid (and amino acid) sequences for fHbp variants are also provided in GenBank.

For purposes of identifying relevant amino acid sequences contemplated for use in the subject fHbps disclosed herein, it should be noted that the immature fHbp includes a leader sequence of about 19 residues. Furthermore, when provided an amino acid sequence the ordinarily skilled person can readily envision the sequences of nucleic that can encode for, and provide for expression of, a polypeptide having such an amino acid sequence.

In addition to the specific amino acid sequences and nucleic acid sequences provided herein, the disclosure also contemplates polypeptides and nucleic acids having sequences that are at least 80%, at least 85%, at least 90%, or at least 95% identical in sequence to such examples of amino acid and nucleic acids. The terms "identical" or percent "identity," in the context of two or more polynucleotide sequences, or two or more amino acid sequences, refers to two or more sequences or subsequences that are the same or have a specified percentage of amino acid residues or nucleotides that are the same (e.g., at least 80%, at least 85%, at least 90%, or at least 95% identical over a specified region), when compared and aligned for maximum correspondence over a designated region, e.g., a $V_E$ or a region of at least about 40, 45, 50, 55, 60, 65 or more amino acids or nucleotides in length, and can be up to the full-length of the reference amino acid or nucleotide sequence (e.g., a full-length fHbp). The disclosure specifically contemplates both naturally-occurring polymorphisms and synthetically produced amino acid sequences and their encoding nucleic acids.

For sequence comparison, typically one sequence acts as a reference sequence (e.g., a naturally-occurring fHbp polypeptide sequence or a segment thereof), to which test sequences are compared. When using a sequence comparison algorithm, test and reference sequences are input into a computer program, sequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information. Further exemplary algorithms include ClustalW (Higgins D., et al. (1994) Nucleic Acids Res 22: 4673-4680).

Some residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is aspartate and glutamate; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

Methods of Production

The fHbps of the present disclosure can be produced by any suitable method, including recombinant and non-recombinant methods (e.g., chemical synthesis). Where the subject fHbp is produced using recombinant techniques, the methods can involve any suitable construct and any suitable host cell, which can be a prokaryotic or eukaryotic cell, usually a bacterial or yeast host cell, more usually a bacterial cell. Methods for introduction of genetic material into host cells include, for example, transformation, electroporation, conjugation, calcium phosphate methods and the like. The method for transfer can be selected so as to provide for stable expression of the introduced fHbp-encoding nucleic acid. The fHbp-encoding nucleic acid can be provided as an inheritable episomal element (e.g., plasmid) or can be genomically integrated.

Suitable vectors for transferring fHbp-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

In one example, the vector is an expression vector based on episomal plasmids containing selectable drug resistance markers and elements that provide for autonomous replication in different host cells (e.g., in both *E. coli* and *N. meningitidis*). One example of such a "shuttle vector" is the plasmid pFP10 (Pagotto et al. (2000) *Gene* 244:13-19).

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding the subject fHbp, may provide for propagating the subject nucleic acids, or both.

Examples of vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgt10, λgt11, λgt18-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

For expression of a subject fHbp, an expression cassette may be employed. Thus, the present disclosure provides a recombinant expression vector comprising a subject nucleic acid. The expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to an fHbp from which the subject fHbp is derived, or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

It should be noted that fHbps of the present disclosure may comprise additional elements, such as a detectable label, e.g., a radioactive label, a fluorescent label, a biotin label, an immunologically detectable label (e.g., an HA tag, a poly-Histidine tag) and the like. Additional elements of fHbp can be provided to facilitate isolation (e.g., biotin tag, immunologically detectable tag) through various methods (e.g., affinity capture, etc.). The subject fHbp can optionally be immobilized on a support through covalent or non-covalent attachment.

Isolation and purification of fHbp can be accomplished according to methods known in the art. For example, fHbp can be isolated from a lysate of cells genetically modified to express a fHbp, or from a synthetic reaction mix, by immunoaffinity purification, which generally involves contacting the sample with an anti-fHbp antibody (e.g., an anti-fHbp mAb, such as a JAR 5 MAb or other appropriate JAR MAb known in the art), washing to remove non-specifically bound material, and eluting specifically bound fHbp. Isolated fHbp can be further purified by dialysis and other methods normally employed in protein purification methods. In one example, the fHbp can be isolated using metal chelate chromatography methods.

Host Cells

Any of a number of suitable host cells can be used in the production of fHbp. In general, the fHbp described herein may be expressed in prokaryotes or eukaryotes, usually bacteria, more usually *E. coli* or *Neisseria* (e.g., *N. meningitidis*) in accordance with conventional techniques. Thus, the present disclosure further provides a genetically modified host cell, which contains a nucleic acid encoding a subject fHbp. Host cells for production (including large scale production) of a subject fHbp can be selected from any of a variety of available host cells. Examples of host cells for expression include those of a prokaryotic or eukaryotic unicellular organism, such as bacteria (e.g., *Escherichia coli* strains), yeast (e.g., *S. cerevisiae*, *Pichia* spp., and the like), and may include host cells originally derived from a higher organism such as insects, vertebrates, particularly mammals, (e.g. CHO, HEK, and the like). Generally bacterial host cells and yeast are of particular interest for subject fHbp production.

Subject fHbps can be prepared in substantially pure or substantially isolated form (i.e., substantially free from other Neisserial or host cell polypeptides) or substantially isolated form. The subject fHbp can be present in a composition that is enriched for the polypeptide relative to other components that may be present (e.g., other polypeptides or other host cell components). Purified subject fHbp can be provided such that the polypeptide is present in a composition that is substantially free of other expressed polypeptides, e.g., less than 90%, usually less than 60% and more usually less than 50% of the composition is made up of other expressed polypeptides.

Host Cells for Vesicle Production

Where a subject fHbp is to be provided in a membrane vesicle (as discussed in more detail below), a Neisserial host cell is genetically modified to express a subject fHbp. Any of a variety of *Neisseria* spp. strains can be modified to produce a subject fHbp, and, optionally, which produce or can be modified to produce other antigens of interest, such as PorA, can be used in the methods disclosed herein.

Methods and vectors to provide for genetic modification of Neisserial strains and expression of a desired polypeptide are known in the art. Examples of vectors and methods can be found in WO 02/09746 and O'Dwyer et al. (2004) *Infect Immun* 72:6511-80. Strong promoters, particularly constitutive strong promoters are of particular interest. Examples of promoters include the promoters of porA, porB, lbpB, tbpB, p110, hpuAB, lgtF, opa, p110, lst, hpuAB, and rmp. In certain embodiments, the Neisserial strain is modified by recombinant techniques to provide for a sufficiently high level of production of the non-naturally occurring fHbp disclosed herein. Such modified strains generally are produced so as to provide for an expression level of the non-naturally occurring fHbp that is 1.5, 2, 2.5 3, 3.5, 4, 4.5, 5, 5.5, 6, 6.5, 7, 7.5, 8, 8.5, 9, 9.5, or 10-fold or greater over fHbp production in the parental cell not genetically modified to express the non-naturally occurring fHbp. In certain embodiments, the parental cell may be genetically modified to knock out the endogenous fHbp and to overexpress the non-naturally occurring fHbp.

Pathogenic *Neisseria* spp. or strains derived from pathogenic *Neisseria* spp., particularly strains pathogenic for humans or derived from strains pathogenic or commensal for humans, are of particular interest for use in membrane vesicle production. Examples of Neisserial spp. include *N. meningitidis, N. flavescens, N. gonorrhoeae, N. lactamica, N. polysaccharea, N. cinerea, N. mucosa, N. subflava, N. sicca, N. elongata*, and the like.

*N. meningitidis* strains are of particular interest for genetic modification to express the subject fHbps and for use in vesicle production. The strain used for vesicle production can be selected according to a number of different characteristics that may be desired. For example, the strain may be selected according to: a desired PorA type (a "serosubtype", as described above), capsular group, serotype, and the like; decreased capsular polysaccharide production; and the like. For example, the production strain can produce any desired PorA polypeptide, and may express one or more PorA polypeptides (either naturally or due to genetic engineering). Examples of strains include those that produce a PorA polypeptide which confers a serosubtype of P1.7,16; P1.19, 15; P1.7,1; P1.5,2; P1.22a,14; P1.14; P1.5,10; P1.7,4; P1.12, 13; as well as variants of such PorA polypeptides which may or may not retain reactivity with conventional serologic reagents used in serosubtyping. Also of interest are PorA polypeptides characterized according to PorA variable region (VR) typing (see, e.g., Russell et al. (2004) *Emerging Infect Dis* 10:674-678; Sacchi C T et al. (1998) *Clin Diagn Lab Immunol* 5:845-55; Sacchi et al (2000) *J. Infect Dis* 182:1169-1176). A substantial number of distinct VR types have been identified, which can be classified into VR1 and VR2 family "prototypes". A web-accessible database describing this nomenclature and its relationship to previous typing schemes is found at neisseria.org/nm/typing/pora. Alignments of certain PorA VR1 and VR2 types are provided in Russell et al. (2004) *Emerging Infect Dis* 10:674-678.

Alternatively or in addition, the production strain can be a capsule deficient strain. Capsule deficient strains can provide vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell enzyme-linked immunosorbent assay (ELISA) using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. (2003) *J. Infect. Dis.* 187:1616-28), as well as methods of identifying and/or generating capsule-deficient strains (see, e.g., Fisseha et al. (2005) *Infect. Immun.* 73:4070-4080; Stephens et al. (1991) *Infect Immun* 59:4097-102; Frosch et al. (1990) *Mol Microbiol.* 4:1215-1218) are known in the art.

Modification of a Neisserial host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Of particular interest are strains that are deficient in sialic acid biosynthesis. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine-6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) *J Bacteriol.* 176:1530-4).

Capsule-deficient strains can also be generated from naturally-occurring strains using non-recombinant techniques, e.g., by use of bactericidal anti-capsular antibodies to select for strains with reduced levels of capsular polysaccharide.

Where the disclosure involves use of two or more strains (e.g., to produce antigenic compositions containing a subject fHbp-presenting vesicles from different strains), the strains can be selected so as to differ in one or more strain characteristics, e.g., to provide for vesicles that differ in the subject fHbp used, PorA, and the like.

Preparation of Vesicles

The antigenic compositions contemplated by the present disclosure generally include vesicles prepared from Neisserial cells that express a subject fHbp. As referred to herein "vesicles" is meant to encompass outer membrane vesicles as well as microvesicles (which are also referred to as blebs).

The antigenic composition can contain outer membrane vesicles (OMV) prepared from the outer membrane of a cultured strain of *Neisseria meningitidis* spp. genetically modified to express a subject fHbp. OMVs may be obtained from *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

The antigenic composition can contain microvesicles (MV) (or "blebs") containing subject fHbps, where the MV or blebs are released during culture of a *Neisseria meningitidis* strain genetically modified to express a subject fHbp. For example, MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of NspA production, where strains that produce higher levels of NspA may be of particular interest (for examples of *N. meningitidis* strains having different NspA production levels, see, e.g., Moe et al. (1999 *Infect. Immun.* 67: 5664). Other strains of interest for use in production of blebs include strains having an inactivated GNA33 gene, which encodes a lipoprotein required for cell separation, membrane architecture and virulence (see, e.g., Adu-Bobie et al. (2004) *Infect Immun.* 72:1914-1919).

The antigenic compositions of the present disclosure can contain vesicles from one strain, or from 2, 3, 4, 5 or more strains, which strains may be homologous or heterologous, usually heterologous, to one another. For example, the strains may be homologous or heterologous with respect to PorA and/or the fHbp from which the subject fHbp is derived. The vesicles can be prepared from strains that express more than one subject fHbp (e.g., 1, 2, 3, or more subject fHbp) which may be composed of fHbp amino acid sequences from different variants (v.1, v.2, or v.3) or subvariants (e.g., a subvariant of v.1, v.2, or v.3).

The antigenic compositions can comprise a mixture of OMVs and MVs presenting the same or different subject fHbps, where the subject fHbps may optionally present epitopes from different combinations of fHbp variants and/or subvariants and where the OMVs and/or MVs may be from the same or different strains. Vesicles from different strains can be administered as a mixture, or can be administered serially.

Where desired (e.g., where the strains used to produce vesicles are associated with endotoxin or particular high levels of endotoxin), the vesicles are optionally treated to reduce endotoxin, e.g., to reduce toxicity following administration. Although less desirable as discussed below, reduction of endotoxin can be accomplished by extraction with a suitable detergent (for example, BRIJ-96, sodium deoxycholate, sodium lauroylsarcosinate, EMPIGEN® BB, TRITON™ X-100, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate.

The vesicles of the antigenic compositions can be prepared without detergent, e.g., without use of deoxycholate. Although detergent treatment is useful to remove endotoxin activity, it may deplete the native fHbp lipoprotein and/or subject fHbp (including lipidated fHbp) by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from *Neisseria* mutants in which lipooligosaccharide or other antigens that may be undesirable in a vaccine (e.g. Rmp) is reduced or eliminated.

Vesicles can be prepared from *N. meningitidis* strains that contain genetic modifications that result in decreased or no detectable toxic activity of lipid A. For example, such strain can be genetically modified in lipid A biosynthesis (Steeghs et al. (1999) *Infect Immun* 67:4988-93; van der Ley et al. (2001) *Infect Immun* 69:5981-90; Steeghs et al. (2004) *J Endotoxin Res* 10:113-9; Fissha et al, (2005) *Infect Immun* 73:4070). The immunogenic compositions may be detoxified by modification of LPS, such as downregulation and/or inactivation of the enzymes encoded by lpxL1 or lpxL2, respectively. Production of a penta-acylated lipid A made in lpxL1 mutants indicates that the enzyme encoded by lpxL1 adds the C12 to the N-linked 3-OH C14 at the 2' position of GlcN II. The major lipid A species found in lpxL2 mutants is tetra-acylated, indicating the enzyme encoded by lpxL2 adds the other C12, i.e., to the N-linked 3-OH C14 at the 2 position of GlcN I. Mutations resulting in a decreased (or no) expression of these genes (or decreased or no activity of the products of these genes) result in altered toxic activity of lipid A (van der Ley et al. (2001) *Infect Immun* 69:5981-90). Tetra-acylated (lpxL2 mutant) and penta acylated (lpxL1 mutant) lipid A are less toxic than the wild-type lipid A. Mutations in the lipid A 4'-kinase encoding gene (lpxK) also decrease the toxic activity of lipid A. Of particular interest for use in production of vesicles (e.g., MV or OMV) are *N. meningitidis* strains genetically modified so as to provide for decreased or no detectable functional LpxL1-encoded protein, e.g., where the *Neisseria* bacterium (e.g., *N. meningitidis* strain) is genetically modified to provide for decreased or no activity of a gene product of the lpxL1 gene. For example, the *Neisseria* bacterium can be genetically modified to have an lpxL1 gene knockout, e.g., where the lpxL1 gene is disrupted. See, e.g., US Patent Publication No. 2009/0035328. The *Neisseria* bacterium can be genetically modified to provide for decreased or no activity of a gene product of the lpxL2 gene. The *Neisseria* bacterium can be genetically modified to provide for decreased or no activity of a gene product of the lpxL1 gene and the lpxL2 gene. Such vesicles provide for reduced toxicity as compared to *N. meningitidis* strains that are wild-type for LPS production, while retaining immunogenicity of subject fHbp.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low Mg++ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. (1994) In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. (1993) Science 259: 361-365; Porro et al. (1998) *Prog Clin Biol Res.* 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Compositions and Formulations

"Compositions", "antigen composition", "antigenic composition" or "immunogenic composition" is used herein as a matter of convenience to refer generically to compositions comprising a subject non-naturally occurring fHbp as disclosed herein, which subject fHbp may be optionally conjugated to further enhance immunogenicity. Compositions useful for eliciting antibodies, e.g., antibodies against *N. meningitidis*, e.g., bactericidal antibodies to *N. meningitidis*, in a human are specifically contemplated by the present disclosure.

Antigenic compositions contain an immunologically effective amount of a subject non-naturally occurring fHbp, and may further include other compatible components, as needed. Compositions of the present disclosure can contain one or more non-naturally occurring fHbps as described above.

Immunogenic compositions contemplated by the present disclosure include, but are not limited to, compositions comprising:

a) a non-naturally occurring fHbp as provided above; and b) a pharmaceutically acceptable excipient, where the fHbp can be provided as recombinant protein and/or in a vesicle-based composition (e.g., OMV).

The compositions can contain additional antigens of interest, such as Porin A, Porin B, NspA, pilin, or other Neisserial proteins. In addition, the antigen compositions of the invention can comprise additional Neisserial antigens such as those exemplified in PCT Publication Nos. WO 99/24578, WO 99/36544; WO 99/57280, WO 00/22430, and WO 00/66791, as well as antigenic fragments of such proteins.

The compositions may contain more than one type of fHbp, where each fHbps may present epitopes from different combinations of fHbp variants and/or subvariants. For example, the composition may contain the non-naturally occurring fHbp as described above and a naturally occurring v. 1 and/or v. 2 fHbp. In another example, the composition may contain the non-naturally occurring fHbp as described above and a mutant v. 1 and/or v. 2 fHbp, in particular where the mutant fHbp has decreased binding to human fH relative to the naturally occurring corresponding fHbp. Such mutants of v. 1 and v. 2 fHbp are described in US2011/0256180, which is herein incorporated by reference. The v.1 and/or v.2 fHbp amino acid sequences can be combined with the non-naturally occurring fHbp amino acid sequence of the present disclosure as separate entities in the compositions of the invention, or within a fusion polypeptide.

In certain cases, the composition may include a vesicle obtained from a *Neisseria* host cell that is genetically modified with a nucleic acid encoding the non-naturally occurring fHbp described above, such that the encoded non-naturally occurring fHbp is produced by the genetically modified host cell, wherein the vesicle comprises the encoded non-naturally occurring fHbp; and a pharmaceutically acceptable excipient.

The host cells may be further modified to express additional antigens of interest, such as Porin A, Porin B, NspA, pilin, or other Neisserial proteins. In addition, the antigen compositions of the invention can comprise additional Neisserial antigens such as those exemplified in PCT Publication Nos. WO 99/24578, WO 99/36544; WO 99/57280, WO 00/22430, and WO 00/66791, as well as antigenic fragments of such proteins.

By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by *Neisseria*, particularly *N. meningitidis*, more particularly Group B, C, or Y *N. meningitidis*. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

Dosage regimen may be a single dose schedule or a multiple dose schedule (e.g., including booster doses) with a unit dosage form of the antigenic composition administered at different times. The term "unit dosage form," as used herein, refers to physically discrete units suitable as unitary dosages for human and animal subjects, each unit containing a predetermined quantity of the antigenic compositions of the present disclosure in an amount sufficient to produce the desired effect, which compositions are provided in association with a pharmaceutically acceptable excipient (e.g., pharmaceutically acceptable diluent, carrier or vehicle). The antigenic composition may be administered in conjunction with other immunoregulatory agents.

Antigenic compositions can be provided in a pharmaceutically acceptable excipient, which can be a solution such as a sterile aqueous solution, often a saline solution, or they can be provided in powder form. Such excipients can be substantially inert, if desired.

In some embodiments, a subject immunogenic composition comprises a subject fHbp present in a vesicle. In some embodiments, a subject immunogenic composition comprises a subject fHbp present in an MV. In some embodiments, a subject immunogenic composition comprises a subject fHbp present in an OMV. In some embodiments, a subject immunogenic composition comprises a mixture of MV and OMV comprising a subject fHbp. Vesicles, such as MV and OMV, are described above.

The antigenic compositions can further contain an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN 80™, 0.5% w/v SPAN® 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% TWEEN™ 80, and 0.5% SPAN® 85 (optionally containing MTP-PE) formulated into submicron particles using a microfluidizer, (b) SAF, containing 10% Squalane, 0.4% Tween 80, 5% PLURONIC®-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+ CWS (Detox™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/ 44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2230221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr Opin Mol Ther 2001 3:15-24; Roman et al., Nat. Med, 1997, 3, 849-854; Weiner et al., PNAS USA, 1997, 94, 10833-10837; Davis et al, J. Immunol, 1998, 160, 810-876; Chu et al., J. Exp. Med, 1997, 186, 1623-1631; Lipford et al, Ear. J. Immunol., 1997, 27, 2340-2344; Moldoveami et al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157, 4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581, i.e. containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally+a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Adjuvants suitable for administration to a human are of particular interest.

The antigen compositions may contain other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of the subject fHbp in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The subject fHbp-containing formulations can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The fHbp-containing formulations can also be provided so as to enhance serum half-life of fHbp following administration. For example, where isolated fHbps are formulated for injection, the fHbp may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Immunization

The present disclosure provides a method of inducing an immune response to at least one Neisserial strain in a mammalian host. The methods generally involve administering to an individual in need thereof an effective amount of a subject immunogenic composition. The present disclosure also provides non-naturally occurring factor H binding protein (fHbp) of the invention for use as medicaments (e.g. as immunogenic compositions or as vaccines) or as diagnostic reagents. The present disclosure further provides the use of nucleic acid or protein of the invention in the manufacture of a medicament for preventing Neisserial (e.g. meningococcal) infection in a mammal.

The fHbp-containing antigenic compositions are generally administered to a human subject that is at risk of acquiring a Neisserial disease so as to prevent or at least partially arrest the development of disease and its complications. An amount adequate to accomplish this is defined as a "therapeutically effective dose." Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The fHbp-containing antigenic compositions are generally administered in an amount effective to elicit an immune response, particularly a humoral immune response, e.g., a bactericidal antibody response, in the host. As noted above, amounts for immunization will vary, and can generally range from about 1 µg to 100 µg per 70 kg patient, usually 5 µg to 50 µg/70 kg. Substantially higher dosages (e.g. 10 mg to 100 mg or more) may be suitable in oral, nasal, or topical administration routes. The initial administration can be followed by booster immunization of the same of different fHbp-containing antigenic composition. Usually vaccination involves at least one booster, more usually two boosters.

In general immunization can be accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An anti-fHbp immune response can be assessed by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like).

The antigenic compositions can be administered to a human subject that is immunologically naive with respect to Neisseria meningitidis. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by Neisseria).

Methods of Screening

In one example, a method of evaluating the efficacy of a subject fHbp in a vaccine composition involves: (a) immunizing a host animal (e.g., a non-human mammalian host animal, such as a rodent, e.g., a mouse) with a composition comprising a fHbp of the present disclosure; and (b) measuring levels of bactericidal antibodies in the host. The subject method may also include assessing the susceptibility of a host animal administered with a vaccine comprising a subject fHbp to a Neisseria bacterium.

In another example, the method can involve making and identifying antibodies elicited by the subject fHbp. The method involves isolating antibodies from the host animal that have binding affinity to the fHbp, contacting a bacterial cell with the isolated antibodies; and assessing binding of the antibody to the bacterial cell. Additional steps may include assessing the competitive binding of the antibody to fHbp with human factor H; assessing the bactericidal activity against a bacterial pathogen when the antibody is administered to an animal contracted with the bacterial pathogen. In some embodiments, the antibody is in an antibody population, and the method can further comprise: isolating one or more antibodies of the antibody population that bind the bacterial cell. A featured aspect is isolated antibody that is bactericidal against the bacterial cell, which may include, for example, complement-mediated bactericidal activity and/or opsonophagocytic activity capable of decreasing the viability of the bacteria in human blood.

Bacterial pathogens of particular interest are N. meningitidis of any or all variant groups, of diverse capsular groups, such as N. meningitidis Serogroup B, N. meningitidis Serogroup C, N. meningitidis Serogroup X, N. meningitidis Serogroup Y, N. meningitidis Serogroup W-135, and the like.

Methods of Evaluating a Response to a FHBP

The present disclosure provides methods for determining the likelihood that a fHbp will elicit a bactericidal response in an individual; and methods of evaluating a variant fHbp for suitability for inclusion in an immunogenic composition.

Determining the Likelihood that a fHbp Will Elicit a Bactericidal Response

The present disclosure provides a method of determining the likelihood that a non-naturally occurring fHbp of the present discolor (e.g., a fHbp present in a Neisserial vaccine) will elicit a bactericidal response in an individual to at least one Neisseria meningitidis strain. The method generally involves determining the ability of antibody, present in serum obtained from an individual who has been immunized with a fHbp, to inhibit binding of fH to fHbp Inhibition of binding of fH to fHbp by the antibody at a level that is at least about 10% higher, at least about 25%, at least about 50%, at least about 75%, at least about 2-fold, at least about 10-fold, at least about 50-fold, at least about 100-fold, or greater than 100-fold, than the level of inhibition of fH to fHbp by a control antibody that inhibits fH binding to fHbp but that does not generate a bactericidal response, indicates that the fHbp is likely to elicit a bactericidal response to at least one Neisseria meningitidis strain.

The degree of inhibition of binding of fH to fHbp by antibody elicited by immunization with a subject fHbp can be determined using an assay as described herein, or any other known assay. For example, the fH and/or the fHbp can comprise a detectable label, and inhibition of fH/fHbp binding can be assessed by detecting the amount of labelled component present in an fH/fHbp complex and/or detecting the amount of label present in free fH and/or free fHbp (e.g., fH or fHbp not in an fH/fHbp complex).

In one example, assays to assess fH binding to an fHbp involve use of fHbp immobilized on a support (e.g., fHbp immobilized on the well of a microtiter plate). A mixture of a fixed concentration of human fH with dilutions of the test antibodies (e.g., antiserum, e.g., from a human or non-human test animal (e.g., mouse) that has received an antibody-eliciting dosage of an immunogenic composition) are added to the wells and incubated for an amount of time sufficient to allow for antibody binding. After washing the wells, bound fH is detected with a specific anti-fH antiserum (e.g., goat or donkey) containing a labeled component, or a secondary labeled antibody (e.g., rabbit anti-goat or anti-donkey anti-serum). Percent inhibition of bound fH can be calculated by the amount of bound fH in the absence of added human or mouse antibody.

In another variation of such assays, binding of fH to live bacteria in the presence or absence of test antisera is assessed by flow cytometry. Bacterial cells are incubated with a fixed concentration of fH (e.g., detectably labeled fH) and different dilutions of test sera containing antibody. The bacteria are washed and bound fH is detected (e.g., as described above).

Thus, the ability of antiserum from an individual immunized with a subject fHbp to inhibit fH/fHbp binding serves as a surrogate for directly assessing bactericidal activity of the antiserum. A method of the present disclosure for determining the likelihood that a subject fHbp will elicit a bactericidal response in an individual can provide information to a clinician or other medical personnel as to whether a particular immunogenic composition has been effective in eliciting a bactericidal response in an individual.

Immunized individuals can have a similar serum IgG anti-fHbp antibody titer by ELISA. Antisera that provides for overall better inhibition of fH binding is indicative of a more effective, better quality anti-fHbp antibody response and will confer greater protection. Thus, for example, if in comparing the anti-Neisserial antibody response in two individuals (by the anti-fHbp antibodies, i.e, a serum dilution of 1:10,000 inhibits compared to a dilution of 1:3000 by the other individual) the individual with the higher inhibitory activity has better quality anti-fHbp antibody that will confer greater protection. The fH inhibition assay is thus a surrogate for complement-mediated bactericidal titer assays, which complement-mediated bactericidal titer assays are generally more time consuming and difficult to measure than fH inhibition.

Evaluating a Subject Non-Naturally Occurring fHbp

The present disclosure provides methods of assessing or predicting the likelihood that a non-naturally occurring fHbp as disclosed herein will be efficacious in eliciting a bactericidal antibody response in an individual. The methods generally involve assessing the ability of antibody specific for the fHbp variant to inhibit binding of fH to fHbp. The strength of inhibition of binding of fH to fHbp by antibody elicited by immunizing with an fHbp variant positively correlates with bactericidal activity of antibody elicited to the fHbp variant. A fHbp variant that elicits antibody that inhibits binding of fH to fHbp at a high serum dilution is considered a suitable candidate for a vaccine for eliciting protection against one or more strains of *Neisseria*.

For example, the present disclosure provides a method of determining the likelihood that a non-naturally occurring fHbp that has lower affinity for human fH than fHbp ID 79 will elicit bactericidal antibodies in an individual to at least one *Neisseria meningitidis* strain. The method generally involves determining the ability of an antibody elicited in a test non-human animal to the non-naturally occurring fHbp to inhibit binding of fH to fHbp Inhibition of binding of fH to fHbp by the antibody elicited to the non-naturally occurring fHbp at a level that is at least about 10%, at least about 25%, at least about 50%, at least about 75%, at least about 2-fold, at least about 10-fold, at least about 50-fold, at least about 100-fold, or greater than 100-fold, higher than the level of inhibition of fH to fHbp by an antibody elicited in the test non-human animal to fHbp ID 79 indicates that the non-naturally occurring fHbp is likely to elicit a bactericidal response to at least one *Neisseria meningitidis* strain.

Suitable test non-human animals include, e.g., mice, rats, rabbits, and the like. The degree of inhibition of binding of fH to fHbp by antibody elicited to a fHbp variant can be determined using an assay as described herein, or any other known assay. Bactericidal activity of an antibody is readily determined using an assay as described herein, or any other known assay.

A subject method for determining the likelihood that a given non-naturally occurring fHbp that has lower affinity for human fH than fHbp ID 79 will elicit bactericidal antibodies in an individual to at least one *Neisseria meningitidis* strain is useful for identifying suitable immunogens (and/or eliminating unsuitable immunogens), e.g., in the course of vaccine development.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1: Generation of Mutant FHbp ID79

Figure 4:
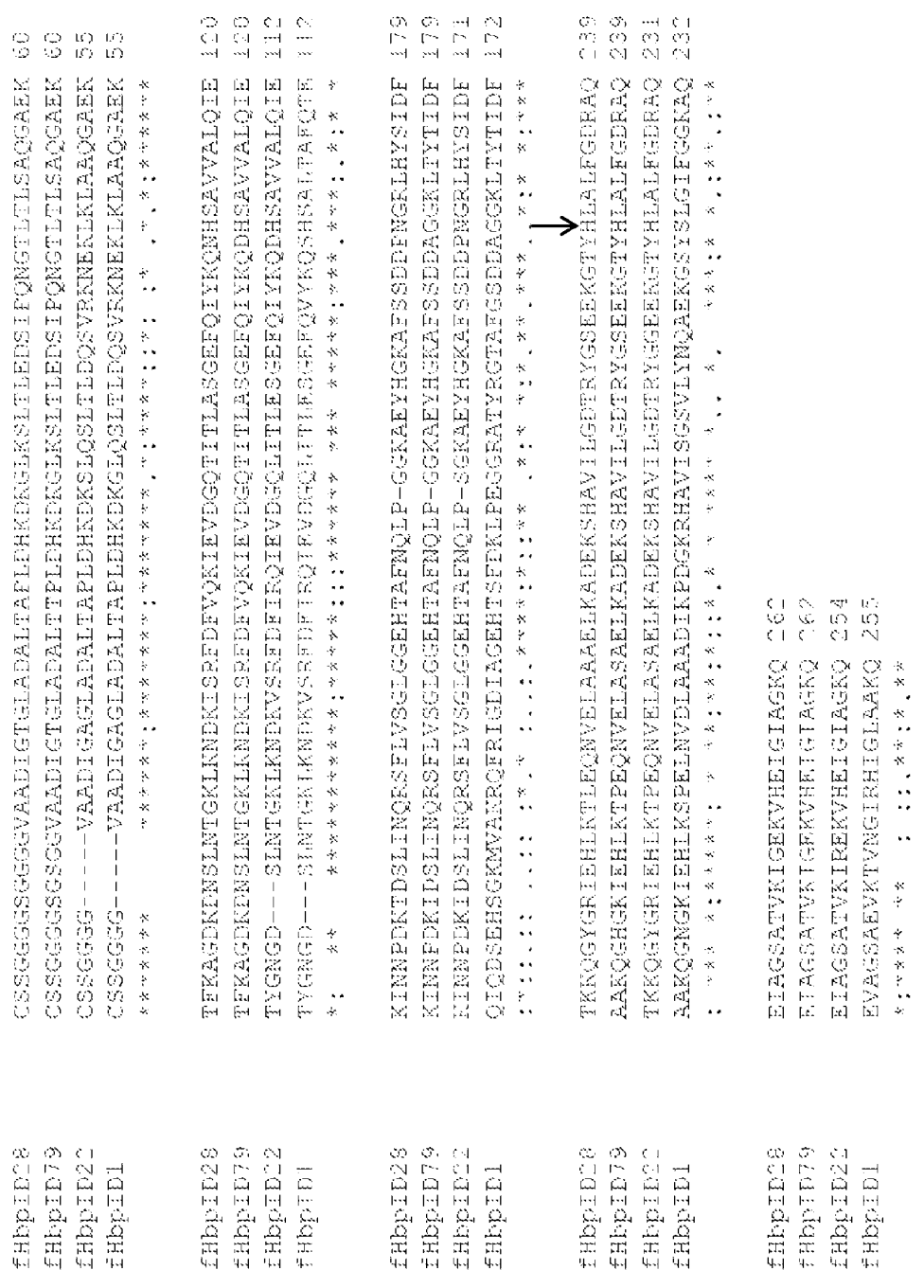

In order to generate mutants of v. 3 fHbp proteins having decreased binding to human factor H, H223A and H223R substitutions were introduced into fHbp ID 79. FIG. 1 shows SDS-polyacrylamide gel indicating size and purity of recombinant factor H-binding protein ID 79 wild-type and mutants. The numbering of the histidine is based on the amino acid position with reference to the amino acid sequence of fHbp ID 1, as shown in the alignment provided in FIG. 4. The histidine 223 position corresponds to histidine 230 in v. 3 fHbp (see FIGS. 4 and 5). The histidine 223 position corresponds to histidine 222 in v. 2 fHbp (e.g. fHbp ID 22; see FIG. 4). Lane 1, Benchmark Ladder (Invitrogen); lane 2 ID 79 wild-type; lane 3 H223R mutant; lane 4, H223A mutant. 2 μg of each of the recombinant fHbps was loaded on the gel. A NuPAGE 4-12% polyacrylamide/Bis-Tris gel was used with MES Running Buffer (Invitrogen). The gel was stained with Simply Blue SafeStain (Invitrogen).

Example 2: Identification of v.3 FHBP Mutant with Decreased fH Binding

Binding of human factor H to ID 79 mutants H223A and H223R by assayed by ELISA. Results are shown in FIG. 2.

Figure 2:
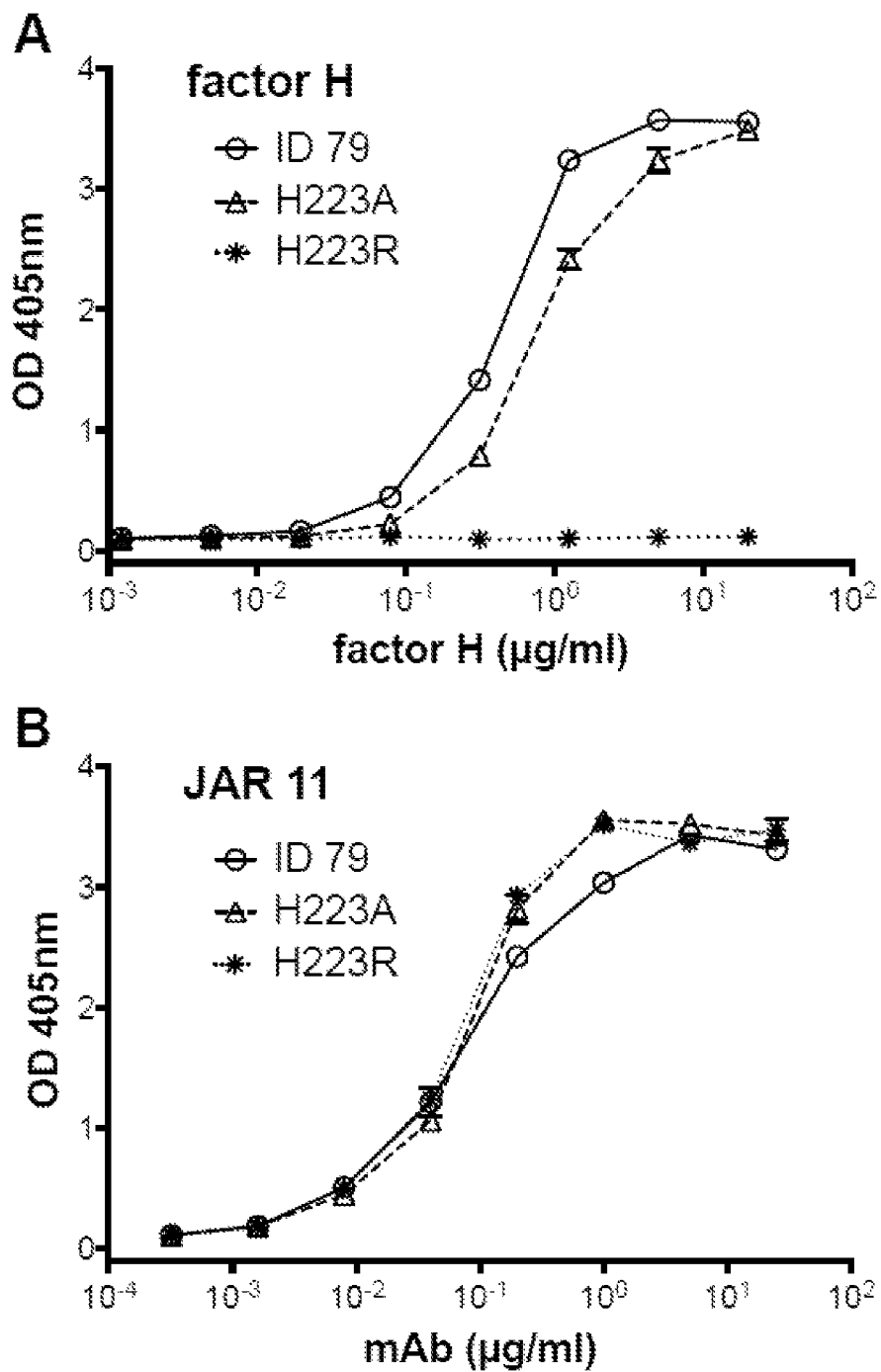
FIG. 2. Binding of human factor H to fHbp ID 79 mutants H223A and H223R by ELISA. Panel A shows binding of human factor H. fHbp ID 79 wild-type (WT), circular symbols; fHbp ID 79 H223A mutant, triangular symbols; fHbp ID 79 H223R mutant, asterisk symbols. Panel B shows binding of a control mAb, JAR 11. Note that the amino acid numbering is based on the numbering of the mature fHbp ID 1. See Example 2 for details.
Figure 3:
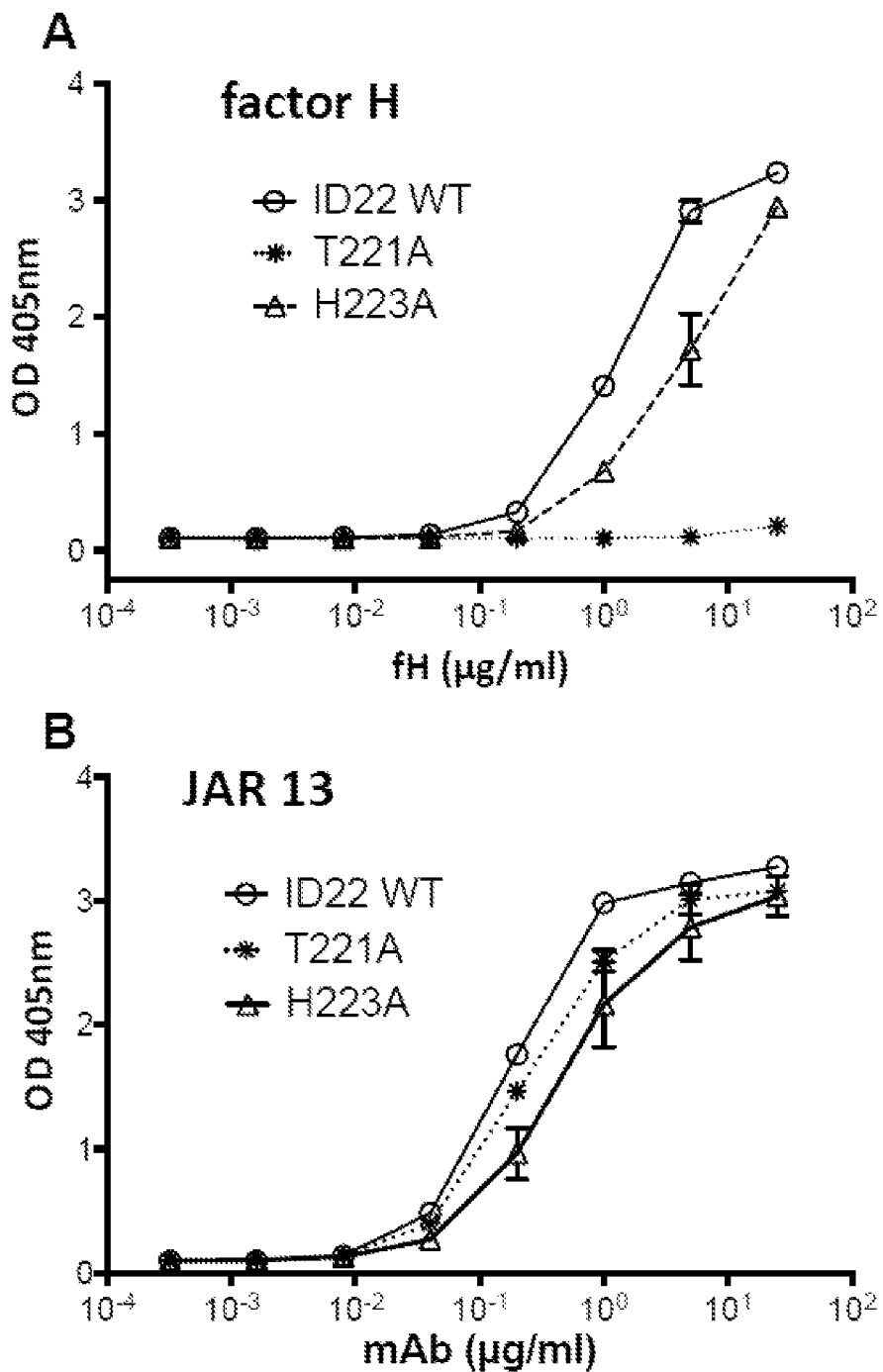
FIG. 3. Binding of human factor H to fHbp ID 22 mutants T221A and H223A by ELISA. Panel A shows binding of human factor H. fHbp ID 22 wild-type (WT), circular symbols; fHbp ID 22 T221A mutant, asterisk symbols; fHbp ID 22 H223A mutant, triangular symbols. Panel B shows binding of a control mAb, JAR 13. Note that the numbering of T221 and H223 is based on the numbering of the mature fHbp ID 1. See Example 3 for details.

FIG. 2, Panel A shows binding of human factor H. fHbp ID 79 wild-type (WT), circular symbols; H223A mutant, triangular symbols; H223R mutant, asterisk symbols. FIG. 2, Panel B shows binding of a control mAb, JAR 11.

Whereas the H223A mutant had only a slight decrease in binding, the H223R mutant showed no detectable binding to human factor H (FIG. 2, Panel A). Binding of a control anti-fHbp mAb, JAR 11, to the H223A and H223R mutant proteins was similar to the wild-type fHbp ID 79 (FIG. 2, Panel B).

Purified recombinant fHbp ID 79 wild-type or mutant proteins (2 μg/ml in PBS) were adsorbed to the wells of a microtiter plate. Non-specific binding was blocked with PBS/1% BSA. For data in Panel A, serial dilutions of purified human factor H (0.0012 to 20 μg/ml) were added to the wells and the plate was incubated for 1 h at room temperature. After washing, sheep anti-human factor H (1:2000 dilution; Panel A) or anti-fHbp mAb JAR 11 (0.00032-25 μg/ml; Panel B) were added to the wells and were incubated for 1 h at room temperature. After washing again, donkey anti-sheep IgG (1:5000; Sigma; Panel A) or goat anti-mouse IgG (1:5000; Sigma Panel B) was added and the plate was incubated for 1 h at room temperature. After washing again, phosphatase substrate (p-nitrophenyl phosphate, 1 mg/ml; Sigma) was added and the optical density at 405 nm was measured after 30 min incubation at room temperature.

Example 3: FHbp Mutant with Decreased fH Binding

T221A and H223A substitutions were introduced individually into fHbp ID 22 (variant group 2). The numbering of the T221 and H223 is based on the amino acid position with reference to the amino acid sequence of fHbp ID 1, as shown in the alignment provided in FIG. 4. T221 corresponds to amino acid position 220 in v. 2 fHbp (e.g. fHbp ID 22) and H223 corresponds to amino acid position 222 in v. 2 fHbp (e.g. fHbp ID 22).

Whereas the T221A mutant showed no detectable binding to human factor H, the H223A mutant showed only a slight decrease in binding compared with the wild-type fHbp ID 22 protein (FIG. 3, Panel A). Binding of a control anti-fHbp mAb, JAR 13, was similar for the wild-type fHbp ID 22 protein, T221A mutant, and H223A mutant (FIG. 3, Panel B).

Binding of human factor H to ID 22 mutants T221A and H223A was assayed by ELISA. FIG. 3, Panel A shows binding of human factor H. fHbp ID 22 wild-type (WT), circular symbols; T221A mutant, asterisk symbols; H223A mutant, triangular symbols. FIG. 3, Panel B shows binding of a control mAb, JAR 13. Purified recombinant fHbp ID 22 wild-type or mutant proteins (2 μg/ml in PBS) were adsorbed to the wells of a microtiter plate. Non-specific binding was blocked with PBS/1% BSA. For data in Panel A, serial dilutions of purified human factor H (0.00032-25 μg/ml) were added to the wells and the plate was incubated for 1 h at room temperature. After washing, sheep anti-human factor H (1:2000 dilution; Panel A) or anti-fHbp mAb JAR 13 (0.00032-25 μg/ml; Panel B) were added to the wells and were incubated for 1 h at room temperature. After washing again, donkey anti-sheep IgG (1:5000; Sigma; Panel A) or goat anti-mouse IgG (1:5000; Sigma Panel B) was added and the plate was incubated for 1 h at room temperature. After washing again, phosphatase substrate (p-nitrophenyl phosphate, 1 mg/ml; Sigma) was added and the optical density at 405 nm was measured after 30 min incubation at room temperature.

Example 4: Bactericidal Response

Wild-type CD-1 mice were immunized with 10 μg of recombinant fHbp ID 79 vaccines with aluminum hydroxide (600 μg per dose; Alhydrogel, Brenntag Biosector) as the adjuvant. A group of six animals was immunized with adjuvant alone (Alum) and groups of eight animals each were immunized with the recombinant fHbp vaccines. Three doses of vaccine were given at three-week intervals and blood was collected three weeks after the third dose. Serum bactericidal assays were performed using serum pools for the adjuvant control group (2 pools from 3 mice each) and individual sera for the fHbp vaccine groups. The bactericidal assay was performed using log-phase bacteria grown in Mueller-Hinton broth containing 0.25% glucose and 0.02 mM CMP-NANA, IgG-depleted human serum as a source of complement. The titers were defined as the reciprocal dilution of serum that resulted in 50% survival of the bacteria after incubation for 60 min relative to negative control wells containing serum from naïve mice. The results are shown in FIG. 7.

What is claimed is:

1. A non-naturally occurring factor H binding protein (fHbp) comprising an amino acid sequence having at least 85% sequence identity to the amino acid sequence of a variant 3 fHbp having an amino acid sequence set forth as SEQ ID NO: 13, the non-naturally occurring fHbp comprising:
   a substitution of the histidine at position 223 of SEQ ID NO: 13 with an amino acid selected from the group consisting of arginine, lysine, phenylalanine, tyrosine, and tryptophan; and
   a serine at position 216 of SEQ ID NO: 13, wherein the numbering of position 223 and position 216 is based on the numbering of the amino acid residues of the mature fHbp ID 1 set forth in SEQ ID NO:1.

2. The non-naturally occurring fHbp of claim 1, wherein the histidine is substituted with arginine.

3. The non-naturally occurring fHbp of claim 1, wherein the non-naturally occurring fHbp comprises an amino acid sequence having at least 90% sequence identity to the amino acid sequence of SEQ ID NO: 13.

4. The non-naturally occurring fHbp of claim 1, wherein the non-naturally occurring fHbp comprises the amino acid sequence of fHbp ID 28 set forth in SEQ ID NO: 4 with the H223R amino acid substitution.

5. The non-naturally occurring fHbp of claim 1, wherein the non-naturally occurring fHbp comprises the amino acid sequence of fHbp ID 175 set forth in SEQ ID NO: 22 with the H223R amino acid substitution.

6. The non-naturally occurring fHbp of claim 1, wherein the non-naturally occurring fHbp comprises the amino acid sequence of fHbp ID 79 set forth in SEQ ID NO: 13 with the H223R amino acid substitution.

7. The non-naturally occurring fHbp of claim 1, wherein the non-naturally occurring fHbp comprises the amino acid sequence of fHbp ID 45 set forth in SEQ ID NO: 11 with the H223R amino acid substitution.

8. An immunogenic composition comprising:
   a) the non-naturally occurring fHbp according to claim 1; and
   b) a pharmaceutically acceptable excipient.

9. The immunogenic composition of claim 8, wherein the non-naturally occurring fHbp is expressed on surface of a vesicle preparation prepared from a *Neisseria meningitidis* strain expressing the non-naturally occurring fHbp.

10. The immunogenic composition of claim 8, wherein the non-naturally occurring fHbp is present as an isolated polypeptide.

11. The immunogenic composition of claim 8, wherein said pharmaceutically acceptable excipient comprises an adjuvant.

12. The immunogenic composition of claim 8, further comprising an additional *N. meningitidis* antigen.

13. An immunogenic composition comprising:
   a) a vesicle obtained from a genetically modified *Neisseria* host cell that is genetically modified with a nucleic acid encoding the non-naturally occurring fHbp according to claim 1 such that the encoded non-naturally occurring fHbp is produced by the genetically modified *Neisseria* host cell, wherein the vesicle comprises the encoded non-naturally occurring fHbp; and b) a pharmaceutically acceptable excipient.

14. The immunogenic composition of claim 13, wherein the vesicle is a native outer membrane vesicle.

15. The immunogenic composition of claim 13, wherein the host cell is genetically modified to provide for decreased or no activity of a polypeptide product of the lpxL1 gene and/or the lpxL2 gene.

16. The immunogenic composition of claim 13, wherein the host cell is further genetically modified to provide for increased expression of a *Neisserial* antigen.

* * * * *